(12) United States Patent
Wang

(10) Patent No.: US 9,295,454 B2
(45) Date of Patent: Mar. 29, 2016

(54) DOUBLE LUMEN OR DOUBLE WIRE ENDOBRONCHIAL ULTRASOUND-GUIDED HISTOLOGY NEEDLE (EBUS)

(71) Applicant: Ko-Pen Wang, Butler, MD (US)

(72) Inventor: Ko-Pen Wang, Butler, MD (US)

(*) Notice: Subject to any disclaimer, the term of this patent is extended or adjusted under 35 U.S.C. 154(b) by 305 days.

(21) Appl. No.: 13/624,368

(22) Filed: Sep. 21, 2012

(65) Prior Publication Data

US 2014/0088456 A1 Mar. 27, 2014

(51) Int. Cl.
*A61B 10/00* (2006.01)
*A61B 10/04* (2006.01)
*A61B 10/02* (2006.01)

(52) U.S. Cl.
CPC ............. *A61B 10/04* (2013.01); *A61B 10/0266* (2013.01); *A61B 2010/045* (2013.01)

(58) Field of Classification Search
CPC .......... A61B 10/0283; A61B 10/0275; A61B 2010/0208; A61B 10/0266; A61B 5/1405; A61B 5/1438; A61B 5/15003
USPC ......... 600/562, 564, 565, 566, 567, 573, 576, 600/578
See application file for complete search history.

(56) References Cited

U.S. PATENT DOCUMENTS

| 4,651,753 A * | 3/1987 | Lifton ............................ 600/564 |
| 4,890,626 A * | 1/1990 | Wang ............................. 600/565 |
| 5,135,492 A * | 8/1992 | Melker et al. .................. 604/508 |
| 5,405,321 A * | 4/1995 | Reeves ............................. 604/44 |
| 5,843,023 A * | 12/1998 | Cecchi ............................. 604/44 |
| 5,997,486 A * | 12/1999 | Burek et al. .................... 600/573 |
| 6,398,743 B1 * | 6/2002 | Halseth et al. .................. 600/585 |
| 6,494,844 B1 * | 12/2002 | Van Bladel et al. ............. 600/567 |
| 6,770,070 B1 * | 8/2004 | Balbierz .......................... 606/41 |
| 6,786,875 B2 * | 9/2004 | Barker et al. ................... 600/585 |
| 6,843,775 B2 * | 1/2005 | Hyun .............................. 600/573 |
| 8,066,648 B1 * | 11/2011 | Mark .............................. 600/566 |
| 8,251,945 B2 * | 8/2012 | Secrest et al. .................... 604/35 |
| 2003/0055373 A1 * | 3/2003 | Sramek et al. ................... 604/19 |
| 2003/0181824 A1 * | 9/2003 | Odland .......................... 600/573 |
| 2005/0027233 A1 * | 2/2005 | Flaherty ....................... 604/6.15 |
| 2005/0096627 A1 * | 5/2005 | Howard ......................... 604/500 |
| 2007/0083129 A1 * | 4/2007 | Mark .............................. 600/566 |
| 2008/0154240 A1 * | 6/2008 | Shippert ........................ 604/542 |
| 2009/0105662 A1 * | 4/2009 | Levedusky et al. ............ 604/192 |
| 2009/0163870 A1 * | 6/2009 | Flagle et al. ............. 604/164.01 |
| 2009/0287190 A1 * | 11/2009 | Shippert ........................ 604/542 |
| 2012/0016265 A1 * | 1/2012 | Peterson et al. ................ 600/580 |
| 2012/0116245 A1 * | 5/2012 | Steiner ........................... 600/563 |
| 2012/0150068 A1 * | 6/2012 | Cucin ............................ 600/566 |

(Continued)

*Primary Examiner* — Sean Dougherty
*Assistant Examiner* — Daniel Cerioni
(74) *Attorney, Agent, or Firm* — Davidson Berquist Jackson & Gowdey LLP

(57) ABSTRACT

An endoscopic needle for collecting tissue, cell and/or fluid specimens from a patient that uses a multi-channel connector having a first channel for accepting a vacuum source that will fluidly connect with a hollow needle at the distal end, and a second channel for receiving a stylet therein, an outer sheath having proximal and distal ends with the proximal end being operatively connected to a lower portion of a leur-lock, an inner tube fluidly connected to the multi-channel connector and an outer needle assembly connected to or as part of the inner tube, an inner needle or a stylet having a proximal end attached to a cap removably connected to the second channel, the stylet having a distal end connected to an inner needle or slidingly positioned within the outer needle, and a fluid pathway from the multi-channel connector to the interior of the outer needle.

13 Claims, 16 Drawing Sheets

(56) References Cited

U.S. PATENT DOCUMENTS

| | | | |
|---|---|---|---|
| 2012/0157879 A1* | 6/2012 | Mark et al. | 600/566 |
| 2012/0191009 A1* | 7/2012 | Hoon et al. | 600/573 |
| 2012/0265094 A1* | 10/2012 | Goldfarb et al. | 600/562 |
| 2014/0128823 A1* | 5/2014 | Odland et al. | 604/319 |

\* cited by examiner

DOUBLE LUMEN OR DOUBLE WIRE ENDOBRONCHIAL ULTRASOUND-GUIDED HISTOLOGY NEEDLE (EBUS)

COPYRIGHT NOTICE

A portion of the disclosure of this patent document contains material which is subject to copyright or mask work protection. The copyright or mask work owner has no objection to the facsimile reproduction by anyone of the patent document or the patent disclosure, as it appears in the Patent and Trademark Office patent file or records, but otherwise reserves all copyright or mask work rights whatsoever.

CROSS-REFERENCE TO CO-PENDING APPLICATIONS

The present invention is related to the following U.S. patents which are all commonly owned with the present application, the entire contents of each being hereby incorporated herein by reference thereto: (1) U.S. Pat. No. 4,532,935, entitled "Bronchoscopic Needle Assembly," Issued on Aug. 6, 1985; (2) U.S. Pat. No. 4,617,940, entitled "Bronchoscopic Needle Assembly," Issued on Oct. 21, 1986; (3) U.S. Pat. No. 4,702,260, entitled "Flexible Bronchoscopic Needle Assembly," Issued on Oct. 27, 1987; (4) U.S. Pat. No. 4,766,906, entitled "Bronchoscopic Needle Assembly," Issued on Aug. 30, 1988; (5) U.S. Pat. No. 4,791,937, entitled "Transendoscopic Needle," Issued on Dec. 20, 1988; (6) U.S. Pat. No. 4,799,494, entitled "Percutaneous Aspiration Lung Biopsy Needle Assembly," Issued on Jan. 24, 1989; (7) U.S. Pat. No. 4,890,626, entitled "Removable Locking Device For Use With Syringes," Issued on Jan. 2, 1990; (8) U.S. Pat. No. 4,966,162, entitled "Flexible Endoscope Assembly," Issued on Oct. 30, 1990; (9) U.S. Pat. No. 5,320,110, entitled "Pleural Biopsy Syringe-Needles," Issued on Jun. 14, 1994; and (10) U.S. Pat. No. 7,147,607, entitled "Transendoscopic Double Needle Assembly," Issued on Dec. 12, 2006; (11) U.S. Pat. No. 7,204,812, entitled "Transendoscopic Needle Assembly," Issued on Apr. 17, 2007.

FIELD OF THE DISCLOSURE

This disclosure relates generally to a double lumen, endobronchial ultrasound guided histology needle assembly for use with a flexible bronchoscope, endoscope or any other type of body cavity scope, and to biopsy devices, and in particular, to needle biopsy devices for collecting tissue, fluid and/or cell samples in conjunction with endobronchial ultra sound (EBUS) procedures.

BACKGROUND OF THE INVENTION

EBUS procedures have been used for many years and allow thoracic surgeons and physicians to use a bronchoscope or endoscope to be inserted and guided through a patient's mouth and trachea and with the scope fitted with an ultrasound processor and a fine gauge aspiration needle is guided through a portion of the scope. Once appropriately positioned, the needle portion of the fine needle aspiration device is advanced into a lymph node or other lesion, the sample is aspirated and the device is removed from the bronchoscope. Such devices pay an increasingly important part in the role of diagnosis and staging of thoracic malignancies.

Conventionally, when biopsies were desired to be taken of the lymph nodes, for example, to aid in the diagnosis of carcinoma, the prior techniques would typically utilize a substantially rigid needle and penetrate the body via percutaneous entry. For example, U.S. Pat. Nos. 3,630,192 and 3,628,524 each to Jamshidi disclose biopsy needles suitable for percutaneous entry. More recently, less invasive flexible biopsy instruments which do not require percutaneous entry have been described. U.S. Pat. No. 4,249,541 to Pratt discloses that a flexible biopsy instrument can be utilized in combination with a fiberoptic bronchoscope.

The foregoing Wang patents relate to a first approach in designing a completely flexible bronchoscopic needle assemblies wherein relatively non-invasive biopsy procedures can be performed utilizing the needle in combination with a fiber optic bronchoscope. The attending physician inserts the bronchoscope into a predetermined one of the patient's natural orifices depending upon the particular organ desired to be biopsied. The needle assembly, which includes an outer catheter and an inner coaxial stylus attached to a retractable needle, is slidably inserted into a receiving passageway of the bronchoscope. The distal end of the needle assembly is urged against tissue, for example the lung's interior wall, and when the needle was pushed out of the needle assembly it would pass into the tissue of the patient, and by using a stabbing force exerted on the proximal end of the stylus (e.g. the end on the exterior of the patient's body), the tissue of the area being penetrated cold be obtained. The bronchoscope enables the attending physician to accurately position the needle and to penetrate the exact location of the desired organ due to the viewing capabilities provided thereby.

A particular problem in utilizing a flexible bronchoscopic needle is that the needle assembly must be flexible enough to allow the physician to maneuver the assembly through the patient's orifice to the target site, but rigid enough to allow penetration of the collection device, such as a needle, into the target tissue. The bronchial wall or hard tumor tissue will need to be penetrated and thus may present significant resistance to entry of the needle. Upon arrival at the target site, the needle assembly, particularly the distal portion of the needle assembly, should be rigid enough to provide a countering pressure against the resistance provided by the bronchial wall or hard tumor tissue or both together. Conventional needle assemblies have not provided a satisfactory means for balancing the necessary flexibility with the desired rigidity as the needle is extended into the target tissue. Thus, a need exists for a needle assembly having flexible characteristics as the assembly is maneuvered through the bronchoscope or a patient's orifice while having rigid characteristics as the needle is inserted into the target tissue.

When obtaining a biopsy of a patient's tissue, it is often desirable for the bronchoscopic needle to penetrate the target site in a perpendicular direction to minimize the length of the penetration into the patients' tissue, and to reduce patient healing time. Another problem with conventional bronchoscopic needles is that the length of the needle may hinder the ability of the needle to enter a target site in a direction perpendicular to the target site wall because the length of conventional needles limits the flexibility of the distal end of conventional flexible bronchoscopic needle assemblies. Thus, a need also exists for a needle assembly having the ability to appropriately penetrate a target site wall in a direction substantially perpendicular to the target site wall.

SUMMARY OF THE INVENTION

The present invention provides a new, flexible, double lumen, or double wire controlled, endobronchial ultrasound guided histology needle assembly that can be used in a standard bronchoscope or endoscope for obtaining biopsy samples. By providing a telescopic needle assembly, which optionally has a retracted length that is shorter than conventional needle assemblies, the present medical device can be more flexible than conventional devices. As a result, the inventive device is useful in a variety of configurations as a surgeon may select, is more easily maneuvered through a scope to site within a patient, while having the desired rigidity characteristics as the needle is telescopically extended and inserted into the patient's target tissue. Additionally, by providing a telescopic needle assembly, which optionally has a retracted length that is shorter than conventional needle assemblies, the present invention provides a medical device having the ability to penetrate a target site in any desired direction.

In one embodiment, the present invention is directed to a medical specimen collection device which includes a flexible outer tubular member or sheath having proximal and distal ends. A second, flexible, plastic inner tubular member, also having proximal and distal ends, is slidably and coaxially received within the outer tubular member, and includes an outer specimen collection needle connected to the distal end thereof as well as a direct connection to the outer needle, through the inner tubular member, to a vacuum source. Further, a flexible inner stylet is provided within the inner tubular member and is connected it a distal end to an inner needle, and a cap is provided at its proximal end and an inner needle is attached to its distal end.

GLOSSARY

As Used Throughout this Document

The phrase "EBUS needle" shall mean a flexible endobronchial ultrasound guided transbronchial needle assembly that includes a dual spring and stylet internal structure and with a Y-shaped proximal end connector.

The term "leur lock or leur lok" shall include any tapered fitting that is a standardized system of small-scale fluid fittings used for making leak-free connections between a male-taper fitting and its mating female part on medical instruments. Luer-Lok™ fittings are securely joined by means of a tabbed hub on the female fitting which screws into threads in a sleeve on the male fitting.

The term "outer tubular sheath" shall include an outer cover or tubular structure for the needle assembly that is preferably formed from a clear material that will support a vacuum or fluid tight path there along, which extends from the Y-connector to the distal end of the needle device and through which a vacuum or fluid path can be formed from the Y-connector to and through a distal end needle.

The term "inner tube or inner tubular member" shall include an elongated member through which a stylet can pass and in which it can slidingly move, and the proximal end is sealed at one portion of the Y-connector and whose opposite end can be formed into a needle or to which a needle can be attached.

BRIEF DESCRIPTION OF FIGURES

The invention is better understood by reading the following detailed description with reference to the accompanying drawings in which.

DETAILED DESCRIPTION

A. Overview

Figure 1:
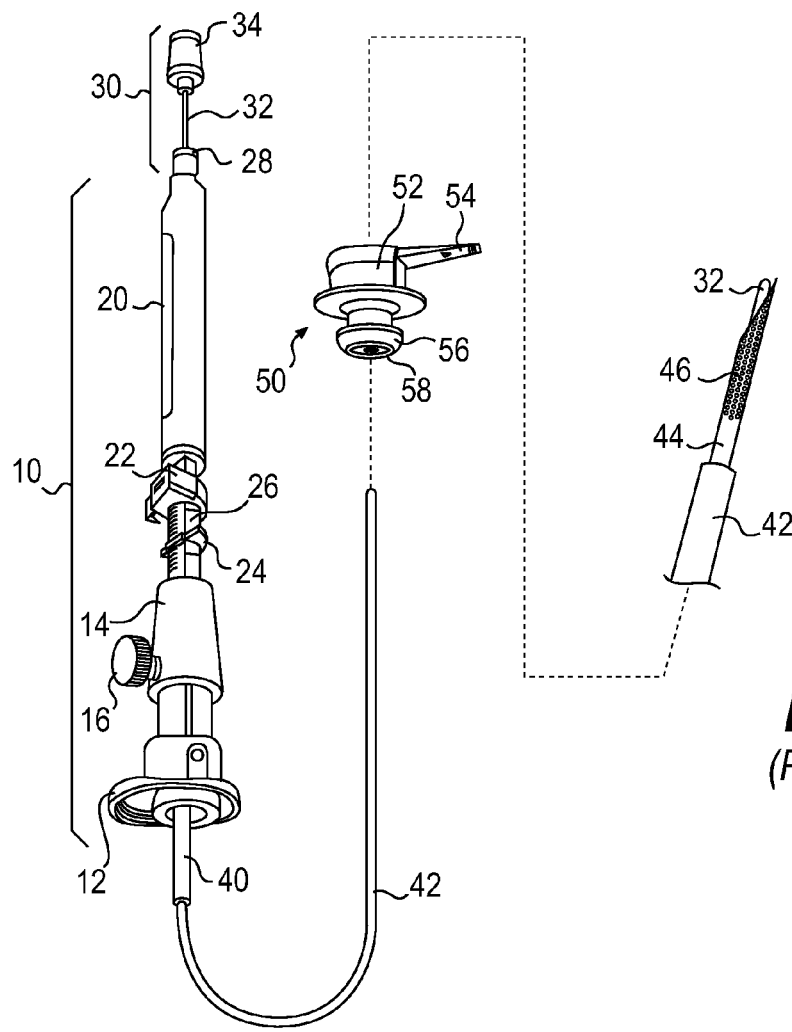
FIG. 1 is a perspective view of a present endoscope/bronchoscope needle.

To gain a better understanding of the invention, a preferred, exemplary embodiment will now be described in detail. Frequent reference will be made to the drawings. Reference numerals or letters will be used throughout to indicate certain parts or locations in the drawings. The same reference numerals or letters will be used to indicate the same parts and locations throughout the drawings, unless otherwise indicated.

B. Environment

The preferred embodiment now described will be with respect to use with a standard bronchoscope and the procedures used when collecting one or more of tissue, cell and fluid specimens. The scale of the embodiment, therefore, is to be understood with respect to this type of article. It is to be understood as well, however, that the invention is applicable to other articles and its scale can vary accordingly.

C. Structure

Figure 2:
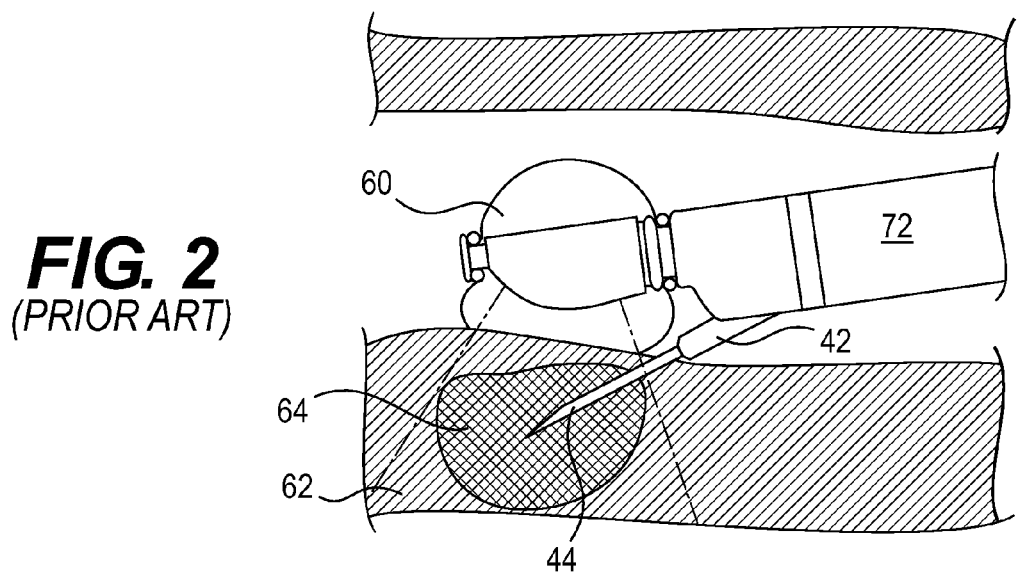
FIG. 2 is a diagrammatic view of the needle of FIG. 1 collecting a sample.
Figure 3:
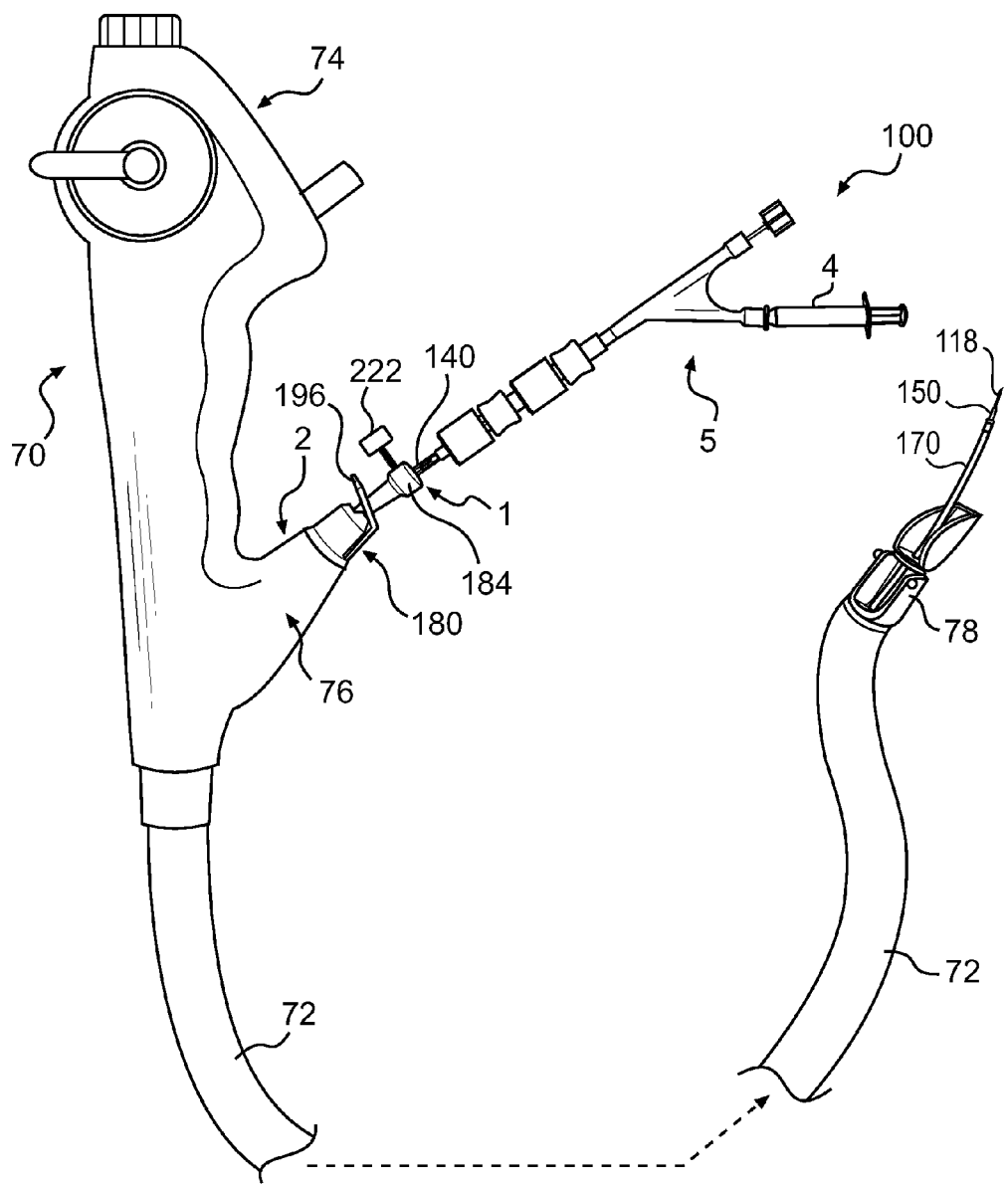
FIG. 3 shows an endoscope with the present invention needle attached.

FIG. 1 shows a single use aspiration needle controller handle 10 for use with an EBUS endoscope, for example a bronchoscope, shown in FIG. 3 at 70. Needle handle 10 includes a locking connector 12 that will lock the needle handle 10 to an attachment section 56 of a single use valve 50 that will fit onto the endoscope 70, for example, at an insertion point 76. Also included with needle handle 10 is a needle sheath 42 will be treaded into the endoscope tubing 72 and the amount of the sheath that will be exposed out of the distal end as shown in FIG. 2 is controlled by a sheath adjusting section 14 whose position relative to needle handle 10 is controlled by a knob 16. The sheath adjusting section is connected to sheath 42 by a boot connector 40.

Needle handle 10 also includes a needle control section 20 that slides along a rod type section 25 and is separately connected to needle 44 that is slidingly retained within sheath 42 and whose sliding position on needle handle 10 is controlled by a needle adjusting lock 22 that can also be moved along the rod section 25 and locked in a desired place to control how much of the needle can project out of the distal end of sheath 42. Rod 25 is secured to the top of the sheath adjusting section 14 and can also include a scale 26 to aid in positioning lock 22. A separate removable lock member 24 can also be used on the scale area 26 to also help in locating lock 22. A stylet 30 includes a wire 32 and a handle or proximal tip 34 and stylet 32 extends along an opening provided within handle 10 and along the whole length of needle 44 to the distal end thereof as shown in FIG. 2. That passageway through which stylet 32 moves is also air tight.

In use, once sheath 42 has been treaded into tube 72 the locking connector 12 will be moved to lock needle 10 relative to valve 50. Then, prior to inserting tube 72 into a patient the sheath adjusting section 14 will be used to move the sheath 42 back and forth to determine how much to permit the distal end of sheath 42 to extend beyond the distal end of tube 72 as shown in FIG. 2. Then, needle control section 20 will be moved to fully with draw needle 44 into sheath 42 and knob 16 will be loosened to permit sheath 42 to be withdrawn into tube 72. Then tube 72 can be introduced into a patient so that the distal end of tube 72 will be positioned adjacent the site for the tissue sample to be taken and a balloon 60 can be inflated to hold the distal end at that point.

Control knob 16 will permit the desired amount of exposure of sheath 42 beyond the distal tip of tube 72 and then knob 16 will be tightened to lock that result. That length will also be viewable via ultra sound. Then, with the needle lock 22 in place needle control section 20 can then be slid back and forth.

Then, to collect a specimen the stylet 32 will be completely withdrawn from within needle 44 and out of needle handle 10 thereby exposing an end 28 of section 20 to which a syringe can be attached. Such a syringe can be used to pull a vacuum at the distal end of needle 44 to pull tissue, cells or fluid into needle 44 as needle 20 to force needle into the area 64 and to then repeatedly penetrate the tissue of that site 64 within a body of tissue 62. As that is needle is being moved the vacuum created by the syringe will aspirate tissue, cell and fluid specimens into needle 44.

At this point the needle control section 20 will be moved proximately to fully withdraw needle 44 into sheath 42 and the needle handle lock 12 will be moved to an unlocked position and the needle handle 10 and the connected sheath 42 will be fully withdrawn from tube 72. To remove any specimens from needle 44 either a syringe can be placed on end 28 to push such specimens out of the distal end of needle 44 or the stylet 32 can be reinserted through needle 44 to push out specimens from the distal end of needle 44. Thereafter, the whole needle handle 10, sheath 42 and needle 44 will be discarded.

FIGS. 4-9 show an embodiment of the present invention, and FIG. 3 shows a needle assembly 100 in place on and endoscope 70 that includes a handle 74, tube section 72 and a distal end thereof 78.

FIGS. 4-7 show needle assembly 100 as including a Y-connector 102 having a first portion 104, a second portion 106, and a depending distal portion 108. Portion 106 can be axially aligned with distal portion 108 so that the transition for a needle, stylet or other device easier to feed there between. It can be also noted that first portion 104 will preferably be positioned at an angle to an axis along which the second portion 106 and the distal portion 108 are axially arranged or aligned, with such an angle for the first portion 104 varying from about 20° to about 90° relative to that axis, or preferably between about 30° to about 45°, and more preferably at about 40°.

The Y-connector 102 is preferably a one piece, integrally formed or molded structure with a hollow interior or passageways that serve to fluidly interconnect the first, second and distal portions thereof. The Y-connector can be molded from any of a variety of plastic or synthetic materials, including, for example, but not limited to a thermosetting resin, a thermoplastic resin, polymers, polypropylene, polyethylene, polycarbonate, polyvinyl chloride, polyamides or polyethylene terephthalate. The Y-connector 102 can have a hollow interior that fluidly interconnects the first, second and distal portions, as noted above, or the first, second and distal portions could be fluidly interconnected by hollow pathways, for example, positioned around a solid central core area.

Portion 104 includes a proximal end 110 formed with a threaded portion that comprises one half of a leur-lock connection so that a conventional syringe or other equipment can be attached thereto in a fluid tight manner.

Portion 106 also includes a proximal end 112 that is also formed with a threaded portion that also comprises one half of a leur-lock fitting on which a matingly threaded cap 114 can screw as the other half of the leur-lock connection. The proximal end of a stylet, a connector or a wire 116 is preferably molded within cap 114. The stylet, connector or wire 116 can be formed from metal, for example, stainless steel, or a stiff plastic material, for example, a polycarbonate.

The distal end 108 of Y-connector 102 could be molded with an insitu tubular orifice or bore, but is preferably molded so as to include a separate tubular member 120, formed from metal or a plastic material like those described above. An outer sheath 170 is molded over or otherwise secured, for example, by a suitable adhesive, to the distal end 108 or to the distal portion 124, or to both, thereby forming a fluid tight connection there between. The outer sheath 170 can also be formed from a plastic material, for example, one of the plastic materials described above.

A leur-lock 124 includes an upper portion 126 and a lower portion 128. A top part 130 of the upper portion 126 is either molded over the exterior of distal end 108 or is secured thereto by a suitable adhesive or by heat welding. The upper portion 126 also includes a hollow interior 132 that extends through a depending tubular portion 133 over which a lower section 135 is rotatably mounted relative to an upper section 131 and tubular portion 133, and the interior of lower section 135 includes threads 137 that will mate with threads 125. A proximal end 134 of tubular member 120 is exposed within the Y-connector 102 and the lower portion is molded within distal end 108 to define an open pathway 136.

A metal tube 138 is attached or secured within the interior space 136 of tubular member 120 so that an open fluid pathway is established through tubular member 120 directed into metal tube 138. The connection between metal tube 138 and tubular member 120 can be accomplished by any of a variety of approaches, including having a force fit there between, use of a suitable adhesive, the precise type depending upon the materials chosen for each element, welding, spot welding, or another approach. Further, it is also possible that the metal tube 138 could be attached over the exterior of tubular member 120. As a further alternative, metal tube 138 could be formed integrally with tubular member 120 with the two being, in that case, a one piece structure. When assembled, the metal tube 138 will pass through the hollow interior 132 of the upper portion 126 as shown. Further, stylet 116 will also pass through the hollow interior of tubular member 120 and thru the hollow interior of metal tube 138.

Figure 4A:
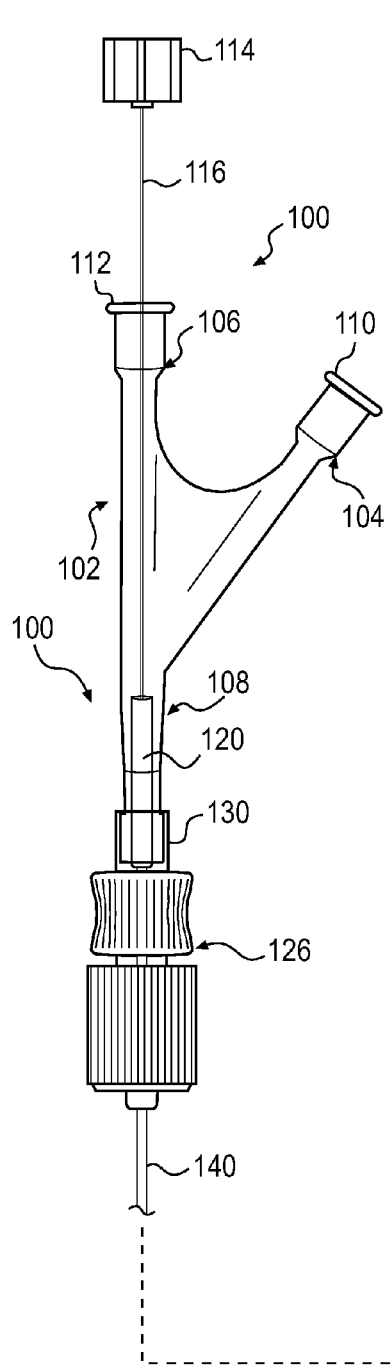
FIG. 4A shows a specimen needle separated into three segments and showing a distal needle in a retracted position, with and end cap on the proximal end of the stylet withdrawn.
Figure 4B:
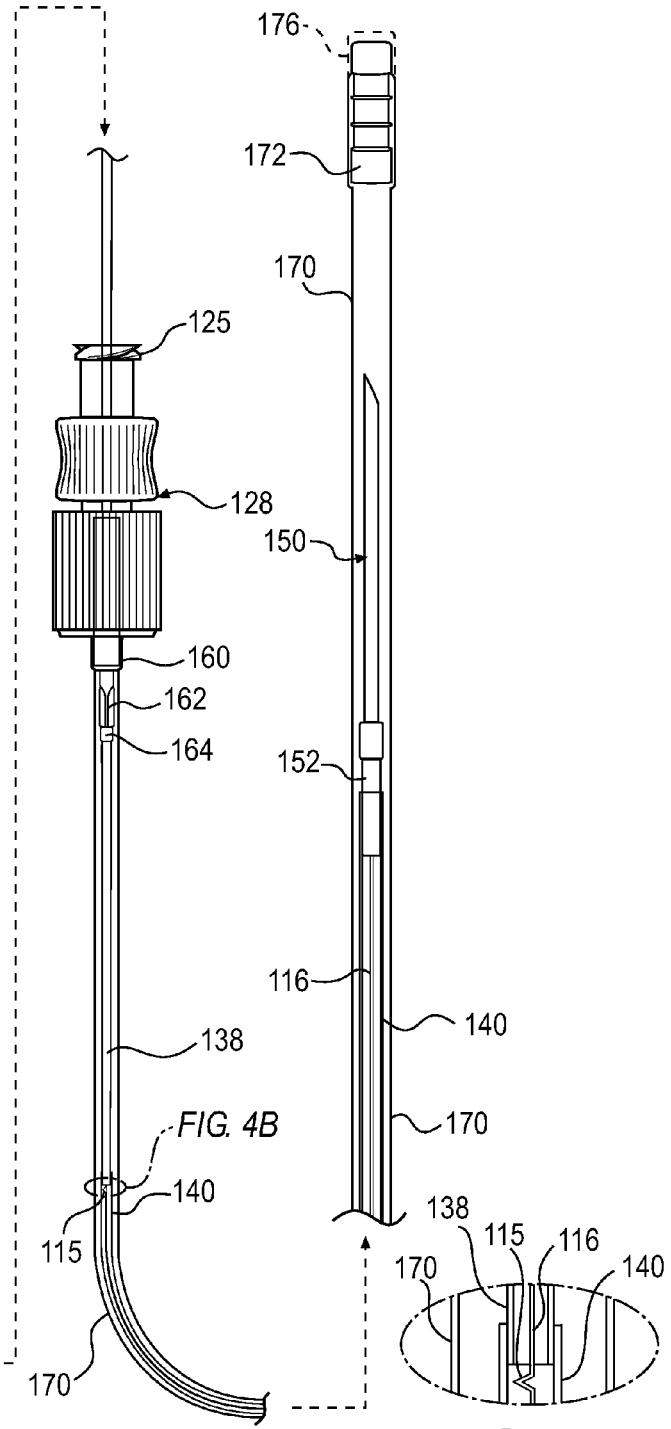
FIG. 4B shows a detailed view from FIG. 4A.
Figure 5:
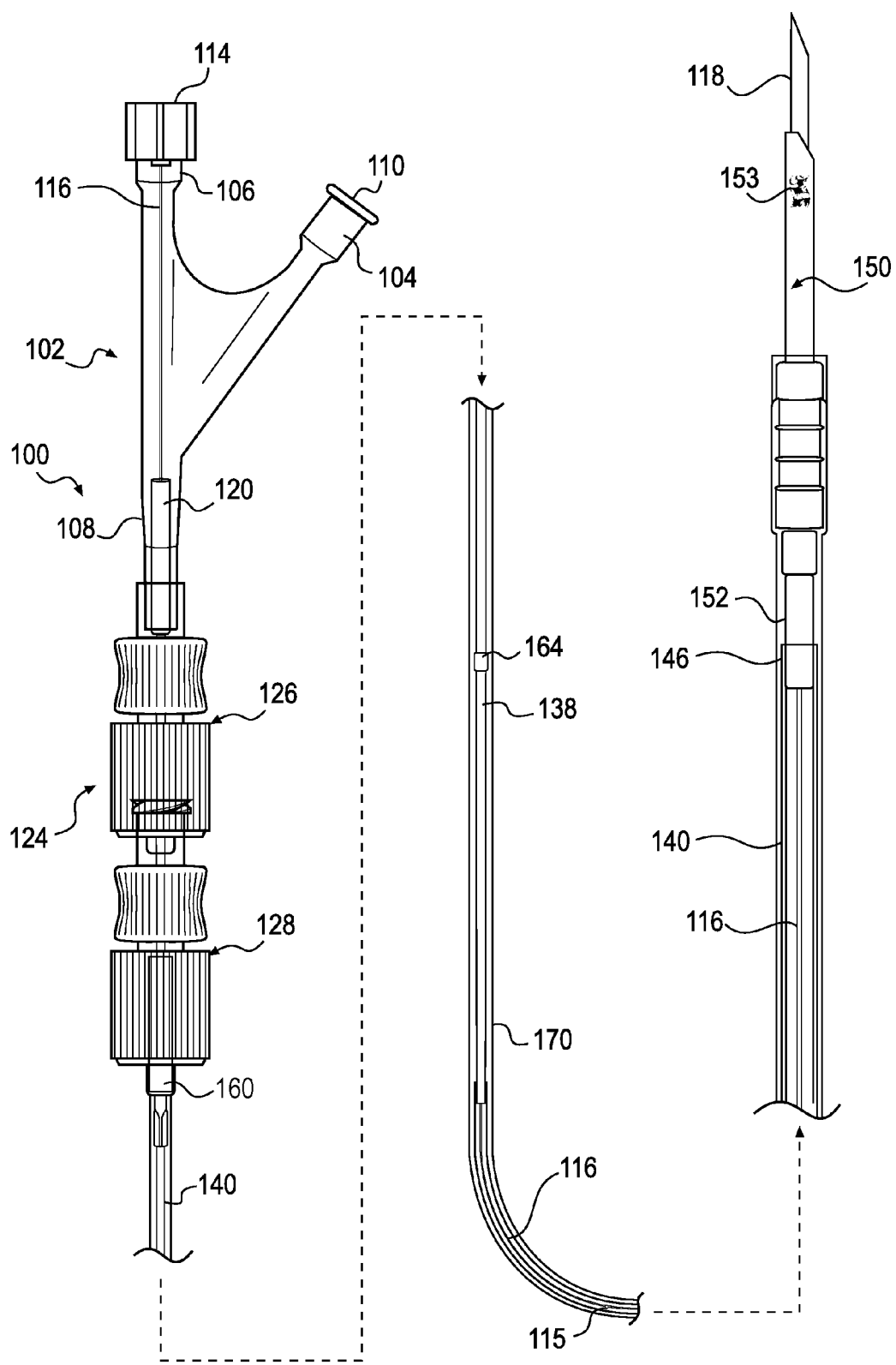
FIG. 5 shows the specimen needle in FIG. 4 having the outer and inner distal needles, both in extended positions.
Figures 7A, 7B:
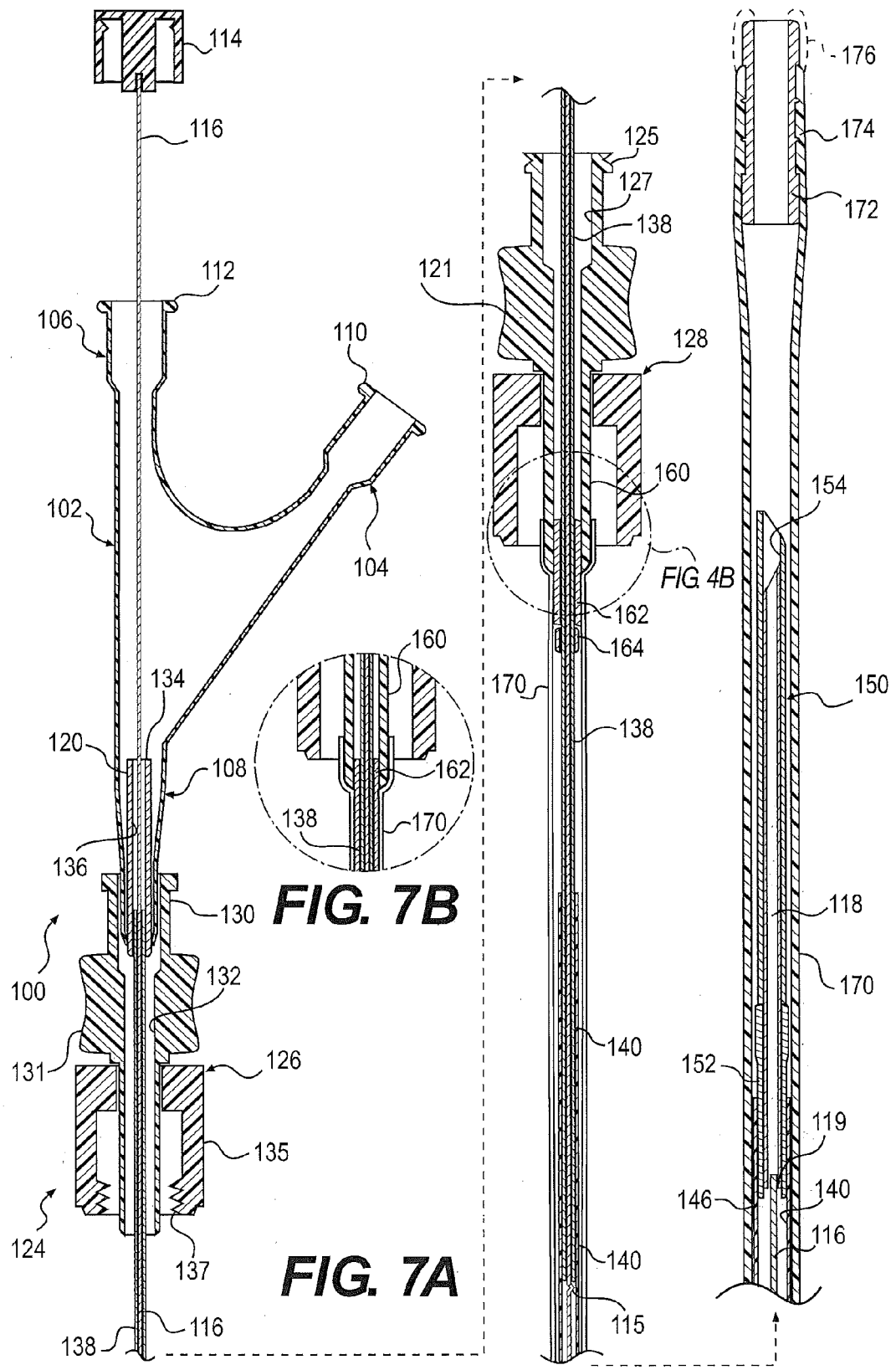
FIG. 7A an enlarged cross-sectional view of the needle shown in FIG. 4.
FIG. 7B shows a detailed view from FIG. 7A.
Figure 8:
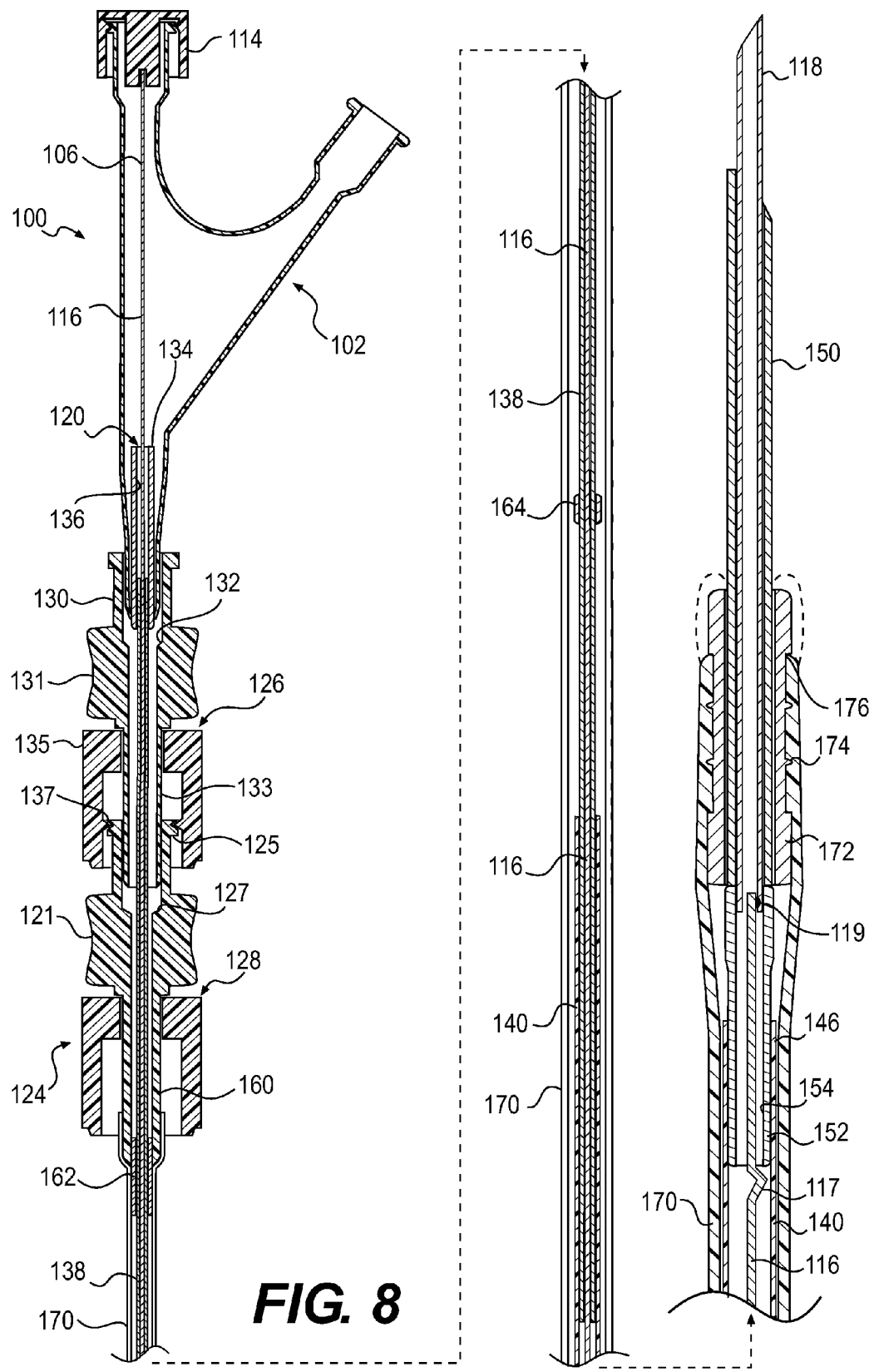
FIG. 8 an enlarged cross-sectional view of the needle shown in FIG. 5.
Figure 9:
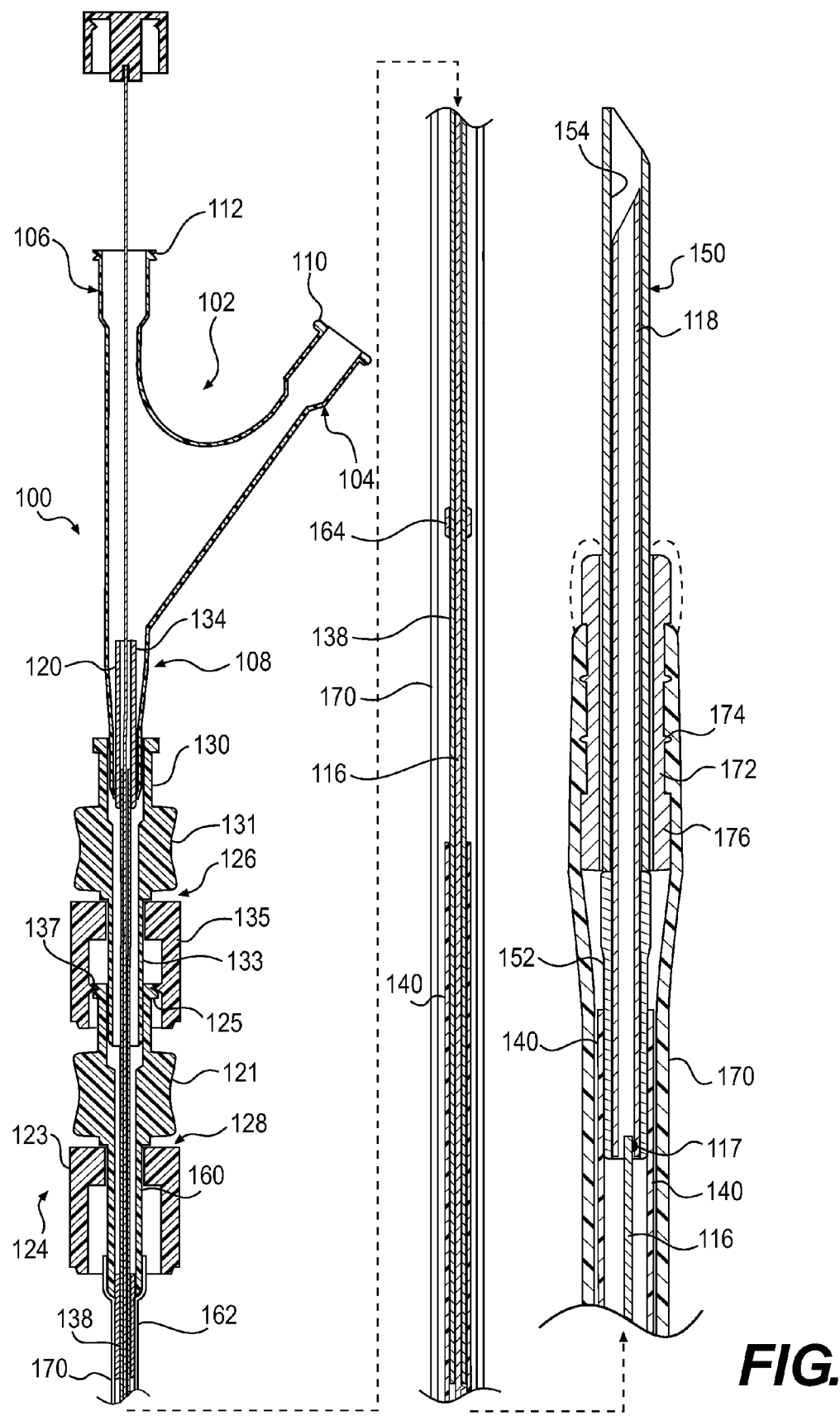
FIG. 9 shows the needle of FIG. 7 with the inner needle partially withdrawn into the outer needle.

As shown in FIGS. 4 and 7, an inner tubular member 140 formed from plastic, Teflon or other similar material will be fit over and secured to a distal end portion of metal tube 138. A distal portion 146 of inner tubular 140 is connected to a proximal end 152 of an outer needle 150, for example a 21 gauge needle, which includes a hollow interior 154, as shown in FIGS. 7-9. The interconnection between needle 150 and the flexible plastic tube 140 can be by use of a suitable adhesive, or another suitable connection approach, so long as a fluid tight seal is formed there between. Thus, a fluid tight pathway extends from within the Y-connector 102 through tubular member 120, through metal tube 138, through the inner tubular member 140 and into the interior of needle 150.

The lower portion 128 of leur lock 124 includes a threaded connector 125 at the top end of an upper section 121, and a hollow internal passageway 127, as shown in FIG. 7, that extends along the length thereof and through an internal depending tube portion 160. A lower section 123 is rotatably mounted about tube section 160 and will rotate relative to the upper section 121 and tube portion 160. A hollow tubular metal extension 162 is secured within the hollow interior of a distal portion of tube portion 160, and it can be secured by a suitable adhesive or by being molded within tube portion 160 or by another suitable approach. An outer tubular sheath 170 formed from Teflon, plastic or similar material is secured over the distal end of the exterior of extension 162, or over both extension 162 and a lower portion of tube portion 160 as shown in FIG. 7. That connection is preferably by way of a suitable adhesive or by a heat welding process and the connection will be such as will provide an air and fluid tight interconnection there between. The outer sheath 170 is also provided at its distal end with a hub 172 to provide a strong and protected distal end. Hub 172 can be force fit into the distal end of sheath 170 or it can be secured by being formed with external ribs 174 or other raised external portions 176 that can grip or interact with the interior of sheath 170 to hold hub 172 in place.

The metal tube 138 along with stylet 116 will be passed through the crimpable metal extension 162 and a stop member 164 will have been fixed onto the exterior of tube 138 at a position to control the amount of pull back or a limit on the ability to withdraw metal tube 138 and the attached inner tube 140, and thereby to control the withdrawal position of outer needle 150. In assembly, once the metal tube 138 has been passed through extension 162, which has an internal dimension large enough to allow stop 164 to pass there through, the bottom portion of extension 162 will be crimped sufficiently to then act as a stop point to prevent further pull back of metal tube 138 when member stop 164 hits the distal crimped end of extension 162.

Stylet 116 includes two kinked or shaped portions one shown at 115 and located more proximally, to provide a withdrawal stop against the distal end of metal tube 138, and a second kink or bent portion 117 that is provided at a position spaced far enough back from the distal end connection to inner needle 118 so that it will interact with the proximal end of outer needle 150 to limit the extended position of the inner needle 118 relative to outer needle 150.

To assemble this needle assembly 100 the cap 114 and the proximal end of wire stylet 116 can be molded together and then threaded through Y-connector 102 and through metal tube 138, previously formed or molded with Y-connector 102. Then the bent or kinked portions 115 and 117 can be formed in stylet 116 and the inner needle 118 can be welded or otherwise secured to the distal end of stylet 116. The Y-connector 102 will be separately formed with metal tube 120 and with metal tube 138 formed and molded in place. The lower portion 128 of leur-lock 124 can be molded with the metal tube 162 as a part of member 160, or alternatively tube 162 can be separately formed and adhesively secured into member 160. Then, with stop member 164 secured at a desired location on the exterior of metal tube 138, needle 118 and stylet 116 as a group can be fed into end 106 of the Y-connector 102 and into and through metal tube 120 and into tube 138 and into the inner tube 140. That combined structure can then be inserted into the hollow interior 127 of the lower portion 128 and through member 162. Once stop member 164 has passed the distal end of member 162 that distal end can be crimped enough to prohibit stop member 164 form being pulled proximally beyond the now crimped distal end of member 162.

Outer needle 150 can have its proximal end secured to the distal end of tube 140 and inner tube 140 can then be cut to a desired length, for example, about 35 to about 60 inches, depending upon the length of inner tube 138, or about 89 to about 153 cm, and fed over the inner needle 118 and along stylet 116 to a point where the proximal end of tube 140 can be force fit over the exterior surface of the distal end of tube 138. Thereafter, the outer sheath 170 can be cut to a desired length, for example, between about 35 to about 60 inches, or about 89 to about 153 cm, the hub 172 can be installed in its distal end. Then, the proximal end of the outer sheath 170 can be pulled over the inner needle and along the tube 140 and have its proximal end secured to the outer tube portion 160 and tube 162 as shown in FIG. 7B. It should be understood that the lengths other than those identified above can be employed depending upon the length of the other equipment being used.

As shown in FIG. 7, where both the proximal and distal ends of assembly 100 are shown in an enlarged cross-sectioned form, cap 114 and stylet 116 are in a withdrawn position thereby withdrawing inner needle 118 inside of outer needle 150 with the kink 115 in stylet 116 in engagement with the distal end of metal tube 138 within the outer sheath 170. Also, the two portions of leur-lock 124 are separated from one another thereby withdrawing metal tube 138 and thereby inner tube 140, stop member 164 is in contact with tubular extension 162 that was crimped and therefore the inner tube 140 will have been pulled proximately so that outer needle 150 is also in a withdrawn position relative to hub 172.

FIG. 8 shows the needle assembly 100 where leur-loc 124 is fitted together and both the outer needle 150 and the inner needle 118 are in an extended position, relative to hub 172. In this condition cap 114 is locked in place on the Y-connector 102 and leur-lock is connected together so that both stylet 116 and metal tube 138 have been pushed to their fullest proximal position, with kink 117 engaging the proximal end of outer needle 150 thereby controlling the extended position of inner needle 118.

FIG. 9 shows almost the same condition as in FIG. 8 except that cap 114 has been twisted and released from threads 112 so that is and stylet 116 have been pulled proximally of the Y-connector 102 thereby pulling the inner needle 118 proximally so that inner needle 118 is now positioned inside the outer needle 150.

Figure 10:
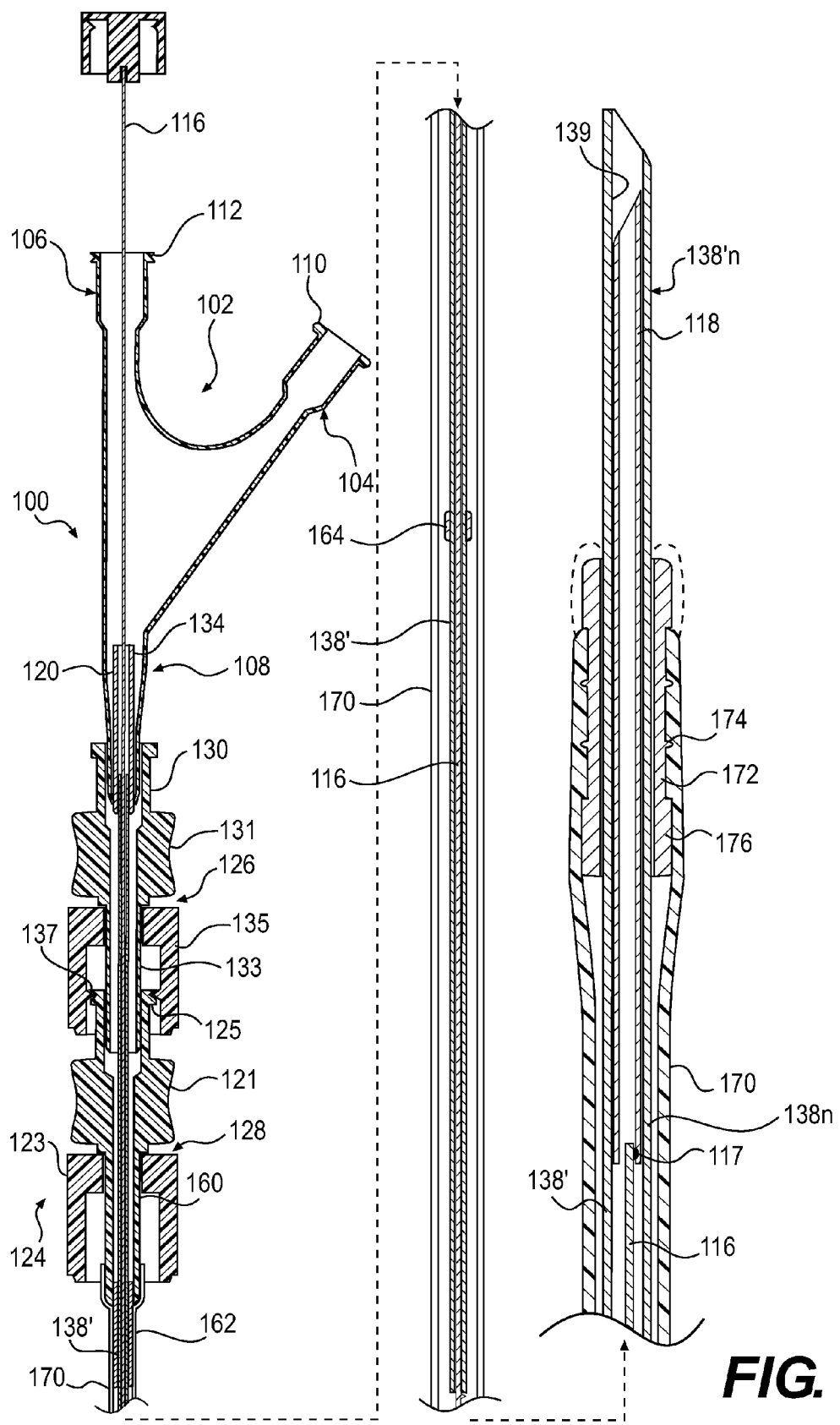
FIG. 10 shows another embodiment of the present invention.

Another needle embodiment of the invention is shown in FIG. 10 where the inner tube 140 is eliminated and the tubular member 138 has been replaced by a stiff metal tube 138' that extends from the connection with the depending tubular portion 160 to a distal end needle tip shown at 138'N. Otherwise, this needle will be similar to that shown in the previous embodiments. This tube 138' can have a 19 gauge size, so that the distal end needle 138'N is formed directly from the distal end of tube 138' will also be a 19 gauge needle, while inner needle 118 remains as a 20 or 21 gauge needle connected to a distal end of stylet 116.

Figure 11:
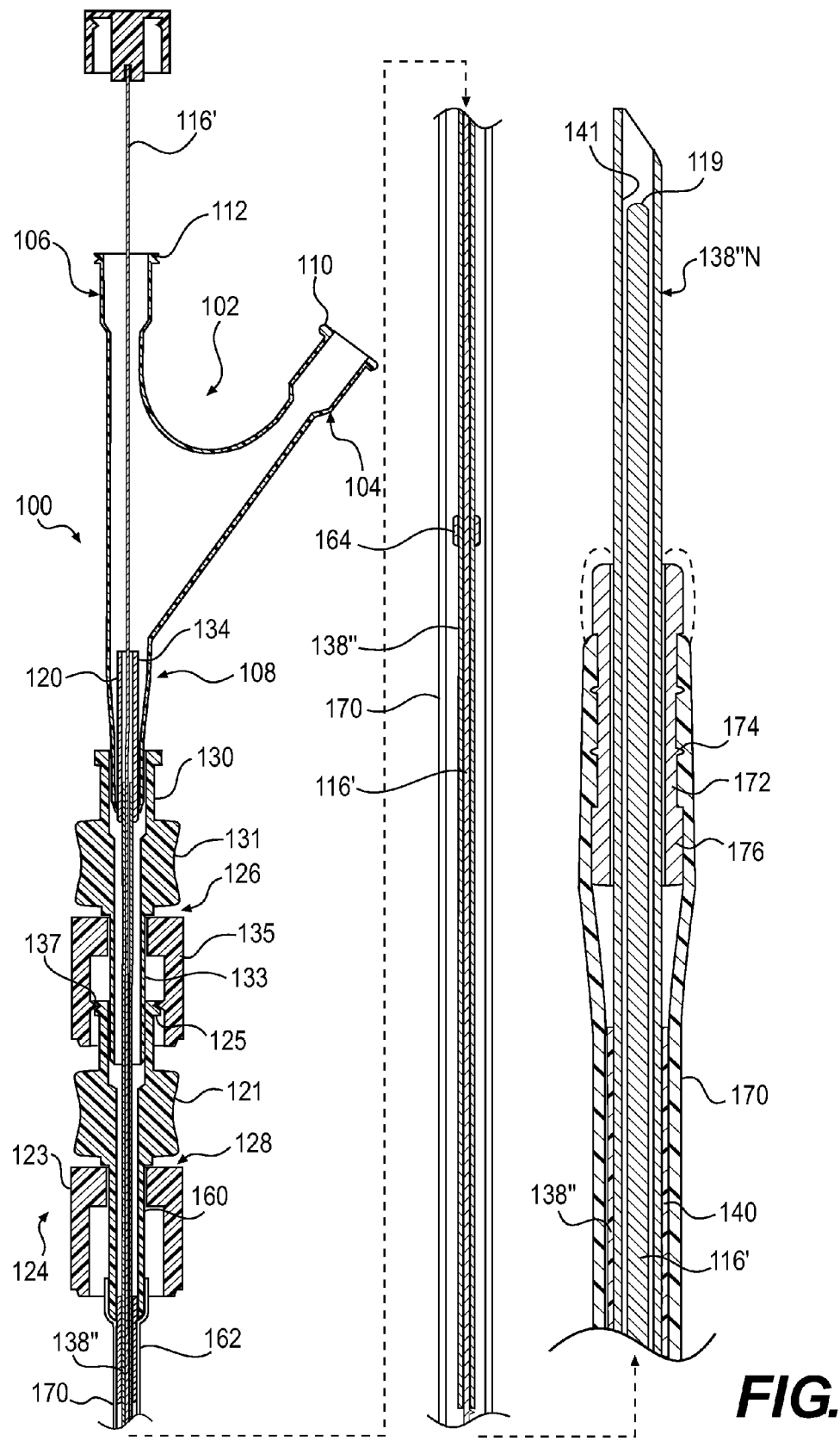
FIG. 11 shows still another embodiment thereof.

FIG. 11 shows another embodiment of the invention where the inner tube 140 has again been eliminated and the tubular member 138 has been replaced by a stiff metal tube 138" that extends from the connection with the depending tubular portion 160 to a distal end needle tip shown at 138"N. Otherwise, this needle will be similar to that shown in the previous embodiments. This tube 138" can also have a 19 gauge size, so that distal end needle 138"N is formed directly from the distal end of tube 138" will also be a 19 gauge needle. But it should be understood that the size of tubular member 138" can be formed from other gauges, such as, for example, a 20 or 21 gauge. In this embodiment the inner needle has been replaced by the distal portion of stylet 116' that is slidingly provided within the outer needle 38"N and preferably has a rounded distal end or tip 119 that will be spaced along the length of tubular member 38" and specifically from the interior 141 thereof by a sufficient gap so that a vacuum or pressure pathway there between is formed to allow fluid to pass there through.

FIGS. 12-16 show another embodiment of the present invention.

Figure 12:
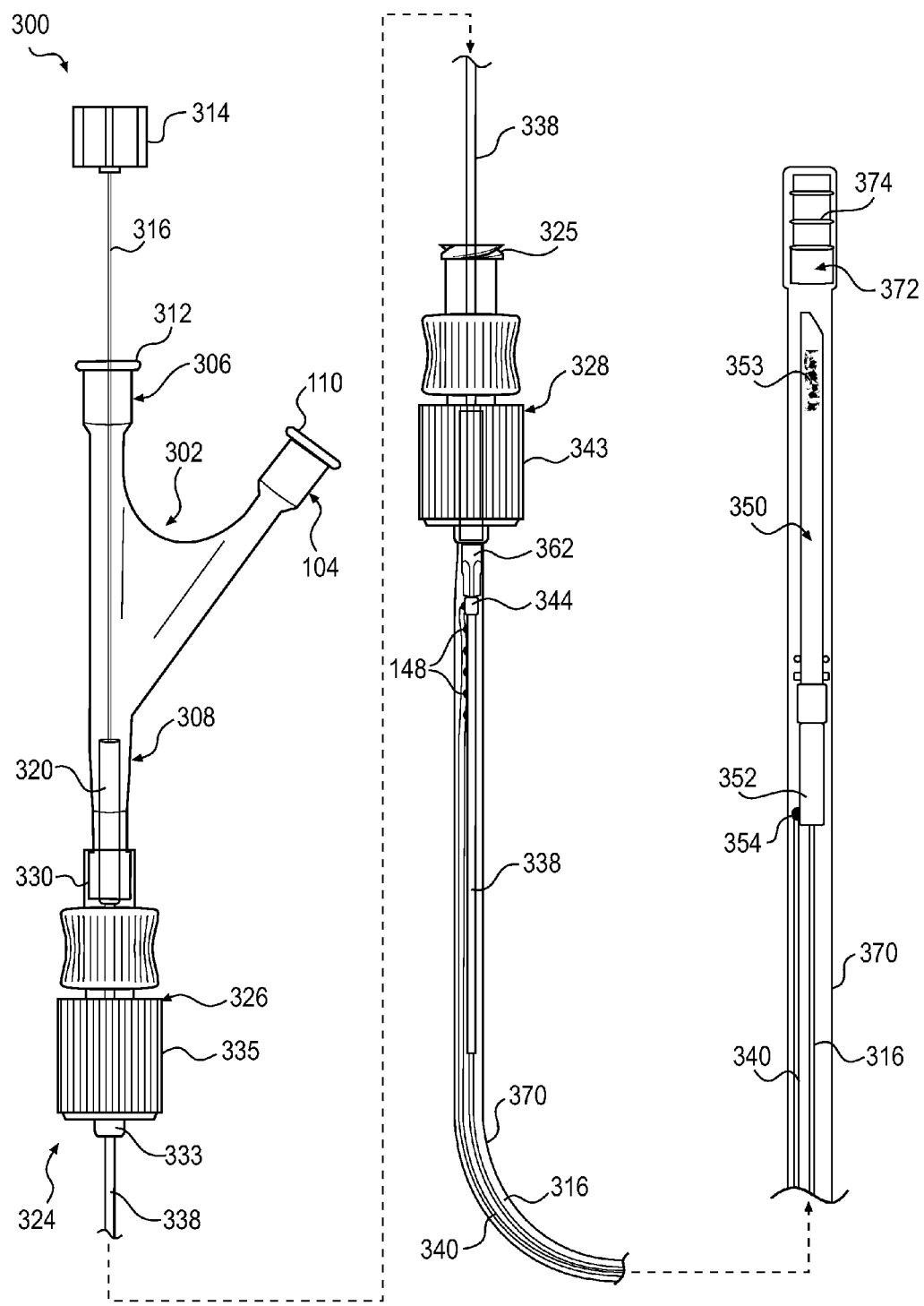
FIG. 12 shows a specimen needle separated into three segments and showing a distal end with an outer needle in a retracted position, and an end cap on the proximal end of the stylet that controls the position of an inner needle in a withdrawn position.
Figure 13:
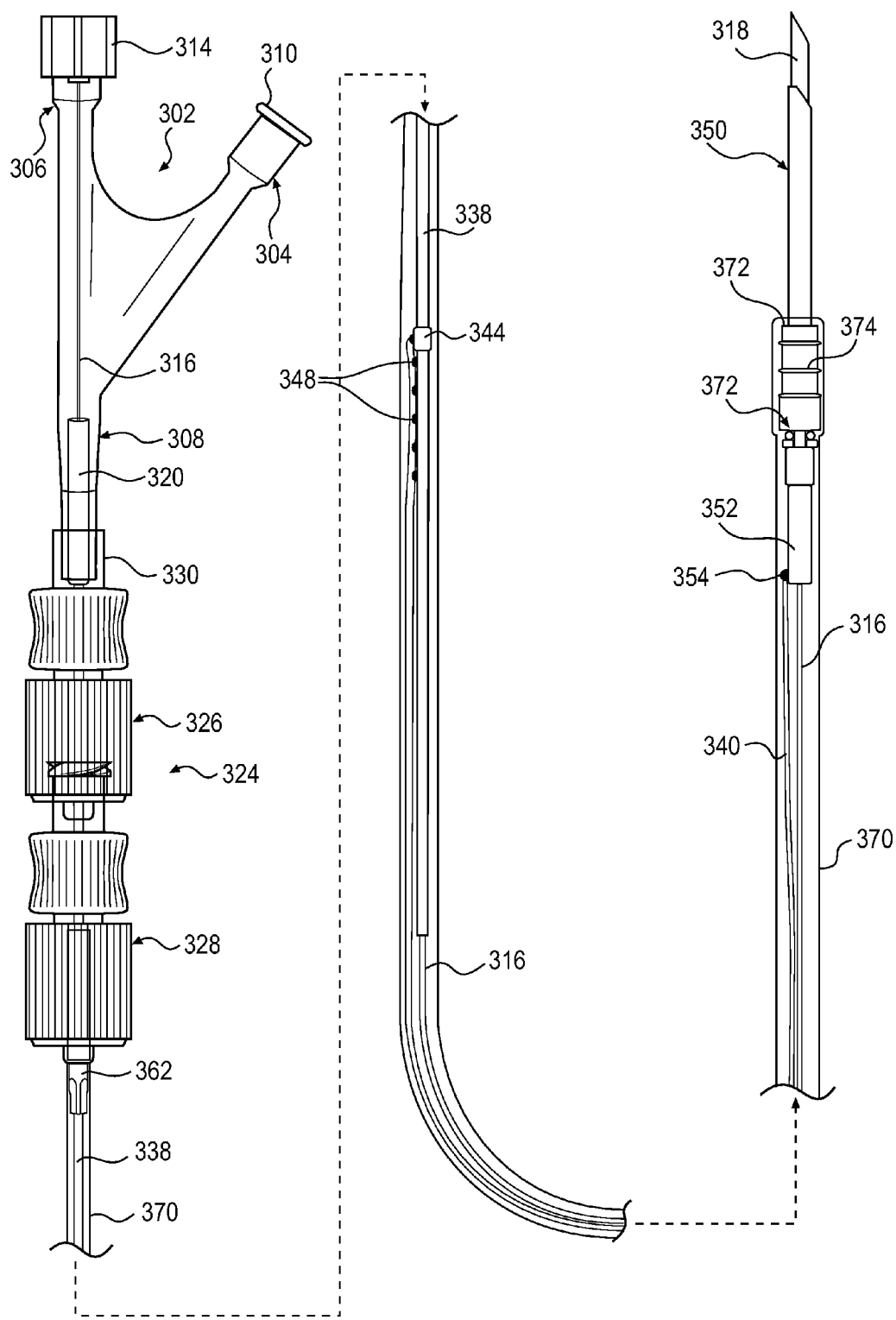
FIG. 13 shows the specimen needle in FIG. 4 having the distal end inner and outer needles in extended positions.

FIG. 12 shows needle assembly 300 as including a Y-connector 302 having a first portion 304, a second portion 306, and a depending distal portion 308. Portion 306 can be axially aligned with distal portion 308 so that the transition for a needle, stylet or other device easier to feed there between. This Y-connector 302 is similar to the previously disclosed Y-connector 102 the description of which is hereby repeated and incorporated.

Portion 304 includes a proximal end 330 formed with a threaded portion that comprises one half of a leur-lock connection so that a conventional syringe or other equipment can be attached thereto in a fluid tight manner.

Figure 6:
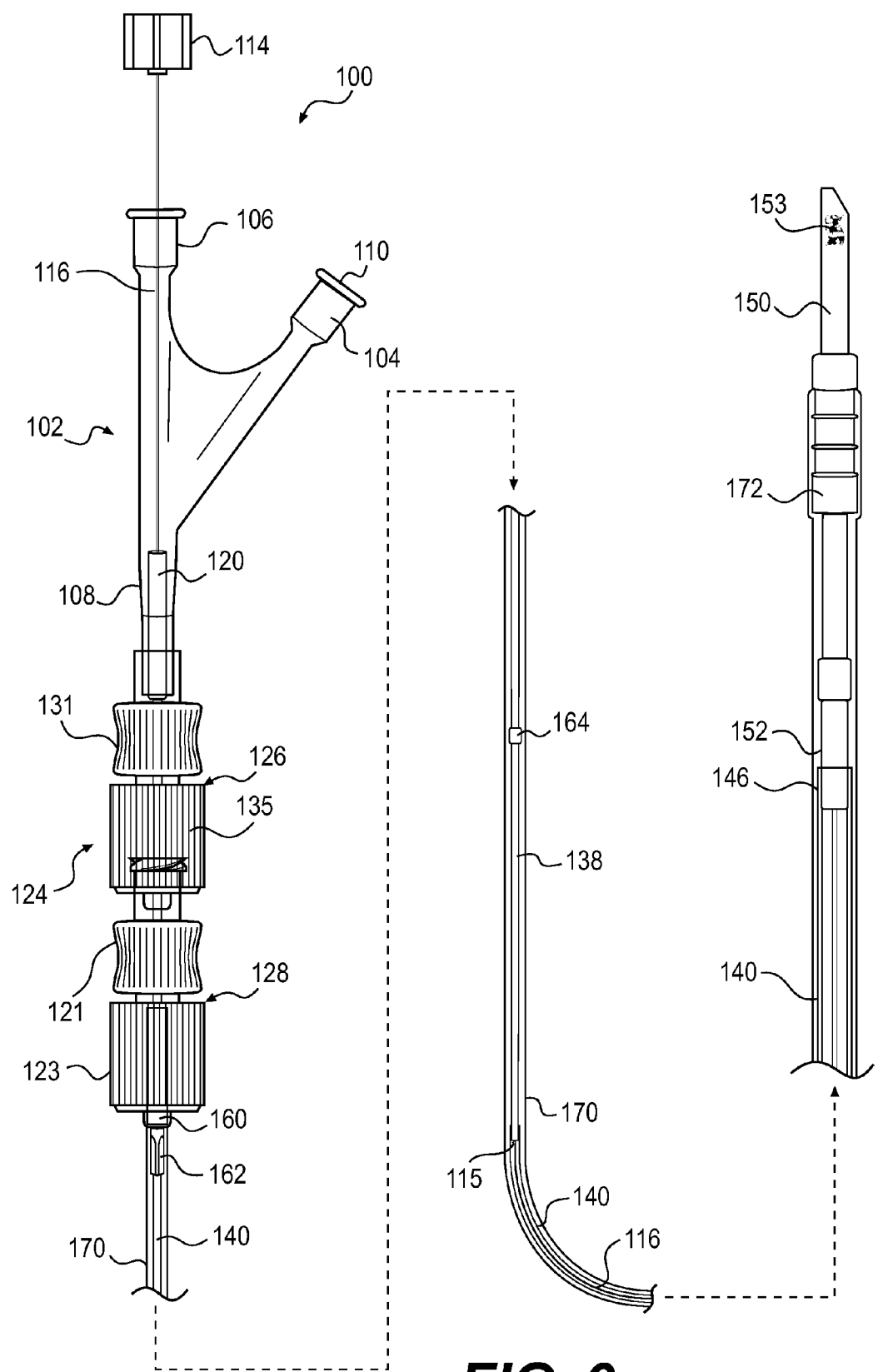
FIG. 6 shows the specimen needle of FIG. 5 with the inner needle at a withdrawn position.

Portion 306 also includes a proximal end 332 that is also formed with a threaded portion that also comprises one half of a leur-lock fitting on which a matingly threaded cap 314 can screw as the other half of the leur-lock connection. A connector, stylet or a wire 316 is also provided and has a proximal end preferably molded within cap 334. The connector or wire 318 can be formed from metal, for example, stainless steel, or a stiff plastic material, for example, a polycarbonate. The distal end of stylet 316 is shown in FIG. 6 as being connected, for example by welding 317 or adhesive to a proximal end of an inner needle 318.

The distal end 308 of Y-connector 302 could be molded with an insitu tubular orifice or bore, but is preferably molded so as to include a O-separate tubular member 320, formed from metal or a plastic material like those described above. An outer sheath 370 is molded over or otherwise secured, for example, by a suitable adhesive, to the distal end 308 or to the distal portion 324, or to both, thereby forming a fluid tight connection there between. The outer sheath 370 can also be formed from a plastic material, for example, one of the plastic materials described above.

Figure 14:
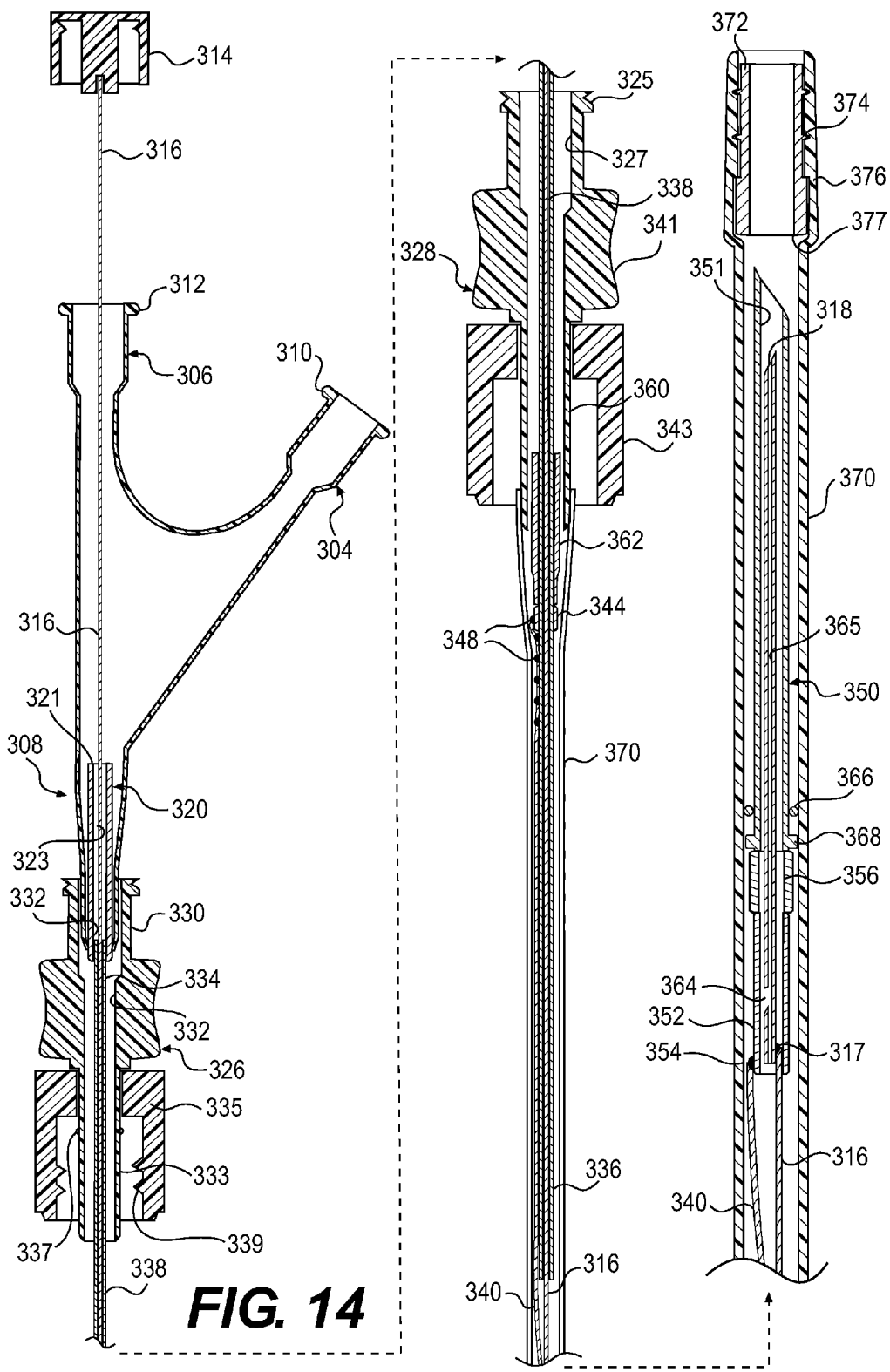
FIG. 14 an enlarged cross-sectional view of the needle shown in FIG. 12.

A leur-lock 324 includes an upper portion 326 and a lower portion 328. A top part 330 of the upper portion 326 is molded over the exterior of distal end 308, and the upper portion 326 also includes a hollow interior 332 with a depending tubular section 333 extending downwardly through member 335 that is rotatably attached by being snap fit over a collar 337. Member 335 includes internally positioned threads 339 to mate with threads 325. A proximal end 323 of tubular member 320 is exposed within the Y-connector 302 and a lower portion thereof is molded within distal end 308 to define an open pathway 323 therein. A metal inner tube 338, for example made of a metal such as Nitinol or other needle forming metal, such a stainless steel, is attached or secured within the interior space 323 of tubular member 320 so that there is an overlap there between and permits an open fluid pathway through tubular member 320 into metal tube 338 to be established. The connection between metal tube 338 and tubular member 320 can be accomplished by any of a variety of approaches, including having a force fit there between, use of a suitable adhesive, welding, spot welding, or another approach, with the precise type of adhesive or approach depending upon the materials chosen for each element. Further, it is also possible that the metal tube 338 could be attached over the exterior of tubular member 320, or that tubular member 320 and inner tube 318 could be formed as a one piece structure. As a further alternative, metal tube 338 could be formed integrally with tubular member 320 with the two being, in that case, a one piece structure. When assembled, the metal tube 338 will pass through the hollow interior 332 of the upper portion 326 as shown in FIG. 14. Further, stylet 316 will also pass through the hollow interior of tubular member 320 and thru the hollow interior of metal tube 338.

Figure 15:
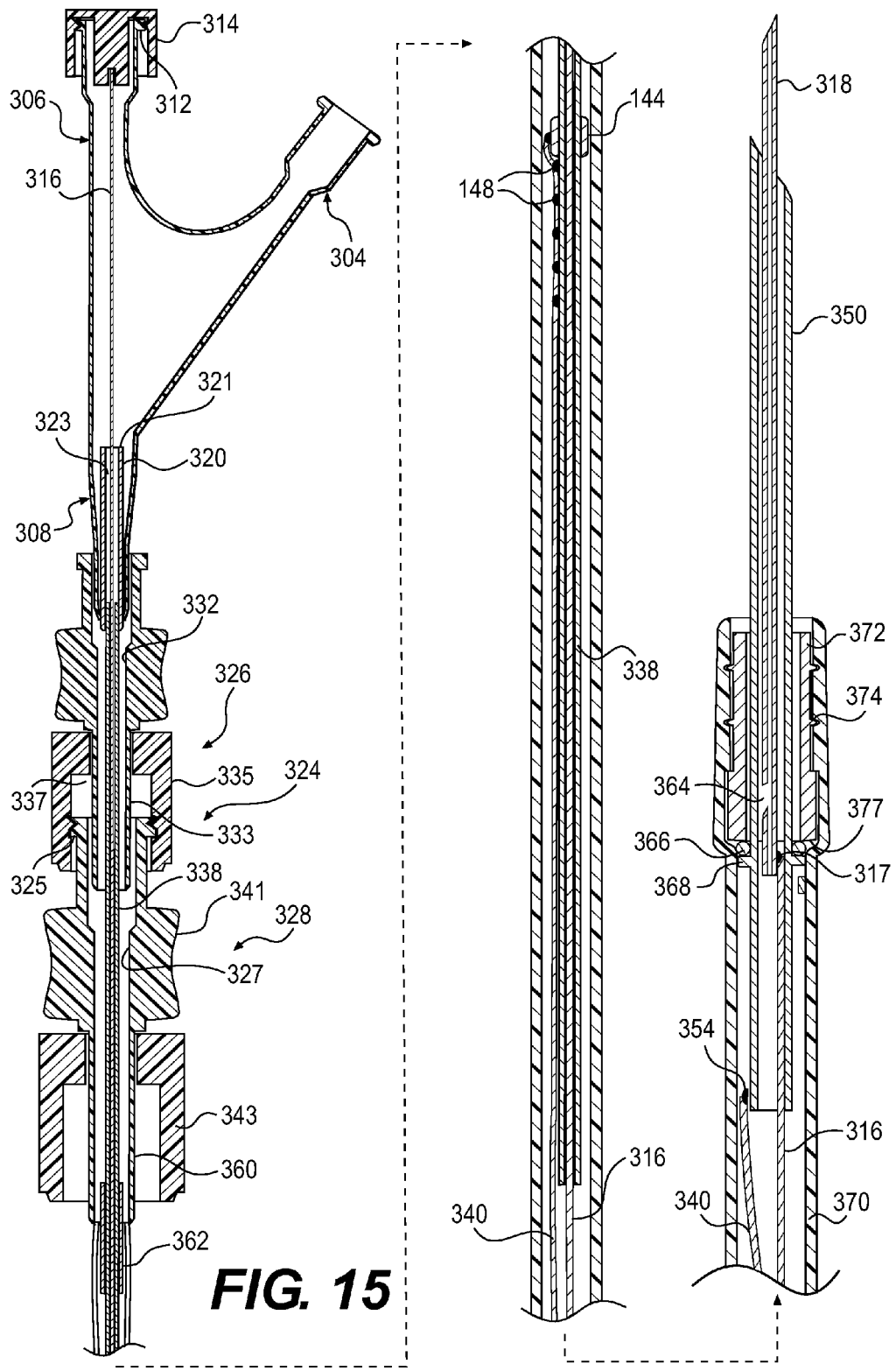
FIG. 15 an enlarged cross-sectional view of the needle shown in FIG. 13.
Figure 16:
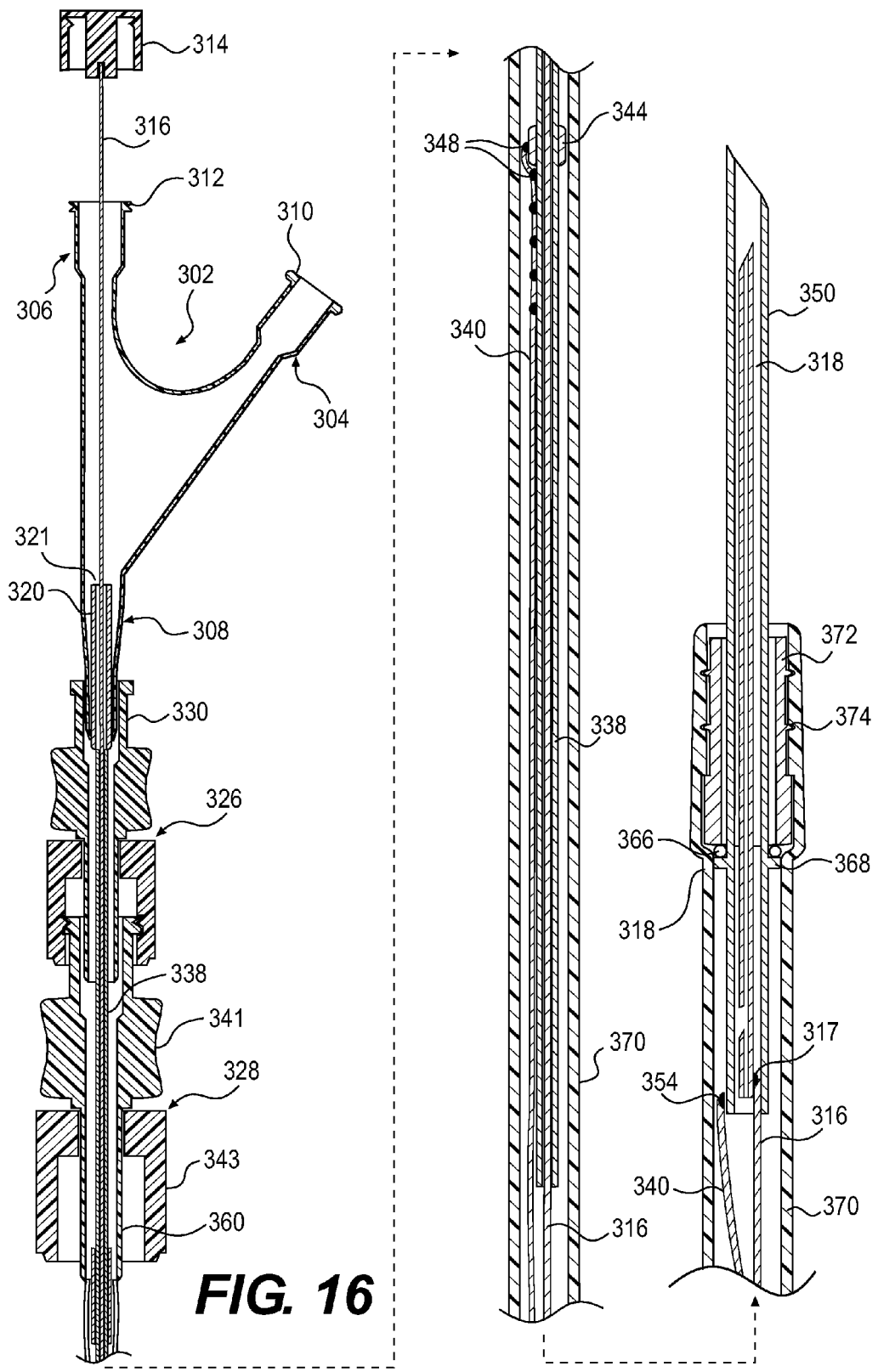
FIG. 16 shows the needle of FIG. 15 with the inner needle withdrawn into the outer needle.

As shown in FIGS. 12 and 14, a second stylet or wire 340 is attached to the exterior of metal tube 338, for example, by welding as shown at 348 and a stop member 344 will be attached to the exterior of metal tube 338, for example, by crimping, welding, or by an adhesive, at a location that will stop the proximal pull back point for metal tube 338, the second wire 340, and an outer needle 350. A distal portion 346 of wire 340 is connected for example by a weld shown at 354 to a proximal end 352 of the outer needle 350 that includes a hollow interior 353, as shown in FIGS. 14-16. The interconnection between needle 350 and wire 340 can, for example, alternatively be by a soldered connection 354, or another suitable connection approach, so long as a secure joint is formed there between.

The distal end portion of outer needle 350 can also be roughened as shown at 351 in FIG. 12, for example by being sanded or otherwise abraded. This will permit a user employing ultra sound or other various electronic or x-ray equipment to easily locate the needle's end making placement and use more precise.

The Y-connector 302 can include a hollow interior and with cap 314 closed over the second portion 306, a fluid tight pathway extends from the first portion 304, through and within the Y-connector 302, through tubular member 320, through metal tube 338, through the outer tubular sheath 370 and into the interior of the outer needle 350 shown at 351.

The lower portion 328 of leur lock 324 includes a top section 343 and a bottom section 343, a threaded connector 325 is provided at the top or proximal end of the top section 343, and a hollow internal passageway 327 that extends along the length thereof and through a depending integrally formed depending tube portion 360. A crimpable metal extension 362 is molded within a distal portion of tube portion 360 and will provide a stop point against which for stop member 344 will abut when pulled there against thereby providing control over the proximal pull of metal tube 338.

An outer tubular sheath 370 is secured to the distal exterior of extension 362, tube 360 or both preferably by a suitable adhesive. The outer sheath 370 is also provided at its distal end with a hub 372 to provide a strong and protected distal end. Hub 372 can be force fit into the distal end of sheath 370 or it can be secured by being formed with external ribs 374 or other raised external portions 376 that can grip or interact with the interior of sheath 370 to hold hub 372 in place.

The metal tube 338 along with stylet 316 will be passed through the extension 362 and a stop member 344 will have been fixed onto the exterior of tube 338. In assembly, once the metal tube 338 has been passed through extension 362, which has an internal dimension large enough to allow stop 344 to pass there through, the bottom portion of extension 362 will be crimped sufficiently to no longer permit stop 344 to enter, but rather will now stop further proximal movement of metal tube 338, the attached wire 340 and consequently outer needle 350.

During specimen collection it is desirable to establish a vacuum or suction within the inner and outer needles, 318 and 350 respectively, to improve specimen collection. As noted above, a fluid tight pathway extends from the first portion 304, then through and within the Y-connector 302, through tubular member 320, through metal tube 338, through the outer tubular sheath 370 and into the interior 351 of needle 350. This vacuum can be achieved, for example, by attaching a syringe to the threads 330 shown for syringe 4 in FIG. 3 on the first portion 304. The vacuum or fluid path then extends into and through tubular member 320 and into the hollow interior of metal tube 338. The fluid path then flows into and through the length of outer sheath 370 to its distal end. There, the proximal end portion of inner needle 318 is provided with an aperture 364 that leads to the hollow interior 365 of inner needle 318. The hollow interior 365 leads to the hollow interior 353 of the outer needle 350 as shown in FIGS. 6-8.

To assure a full or desired vacuum is established within hollow outer needle 350 an O-ring 366 is provided so as to be positioned between the proximal end 377 of hub 372 and a compression collar 368 that extends around the exterior of outer needle 350, as shown in FIG. 6. Alternatively, the outer needle 350 could be provided with a circumferentially extending wall 378 pre-formed on outer needle 350 as shown in phantom in FIG. 8.

To assemble needle 300 the cap 314 end proximal end of stylet 316 can be pre formed, as can the Y-connector 302 with tubular section 320. Metal tube 338 can be secured to the tubular member 320 and the upper leur-lock portion 326 can be secured to distal end 308 of the Y-connector 302, for example, by a suitable adhesive. Then stylet 316 will be threaded into and through the second portion 306 of the Y-connector and metal tube 338 and the second wire 340 can be welded in place. If the stop member 344 has not been previously attached at a desired location, the chosen amount of outer needle pull back, proximally, can be determined and stop member 344 will be secured to metal tube 338 at the desired point to provide that proximal pull back limit. Also, extension 362 will be crimped to act as a stop point therefore.

Needles 318 and 350 can then be attached to the cut distal end of wires 316 and 340, respectively. Inner needle 318, for example, can be a 22 gauge needle, that will be inserted within outer needle 350 which may be, for example, a 20 gauge. Then, O-ring 366 will be placed over outer needle 350 and the outer sheath 370 with hub 372 already installed therein will have been cut to a desired length and slid over the outer needle 350, along wires 316 and 340 and then be mounted over and secured to extension 362 and/or tube portion 360. This will cumulatively result in the needle structure depicted in FIG. 6.

As shown in FIG. 6, where both the proximal and distal ends of assembly 300 are shown in an enlarged form, cap 314 and stylet 316 are in a withdrawn position, and the two portions of leur-lock 324 are separated thereby withdrawing metal tube 338 and therefore wire 340 so that the inner and outer needles 338 and 350 are both in a withdrawn position relative to hub 372.

FIG. 15 shows the needle assembly 300 where the outer needle 350 and the inner needle 318 are both in a fully extended position, relative to hub 372. In this condition cap 314 is locked in place on the Y-connector 302 and leur-lock 324 has both section 326 and 328 connected together. In that arrangement, stylet or wire 316 and wire 340 have both been pushed to their fullest distal position thereby fully extending needles 318 and 350, respectively.

FIG. 16 shows outer needle 350 still in its extended position, but cap 314 has been twisted loose from the second portion 306 and pulled proximally of the Y-connector 302 thereby pulling stylet 316 and the inner needle 318 proximally with inner needle 318 now positioned inside the outer needle 350. However, a vacuum or fluid path to the interior of the outer needle 350 remains open through the aperture 364 and the hollow interior of inner needle 318.

Figure 18:
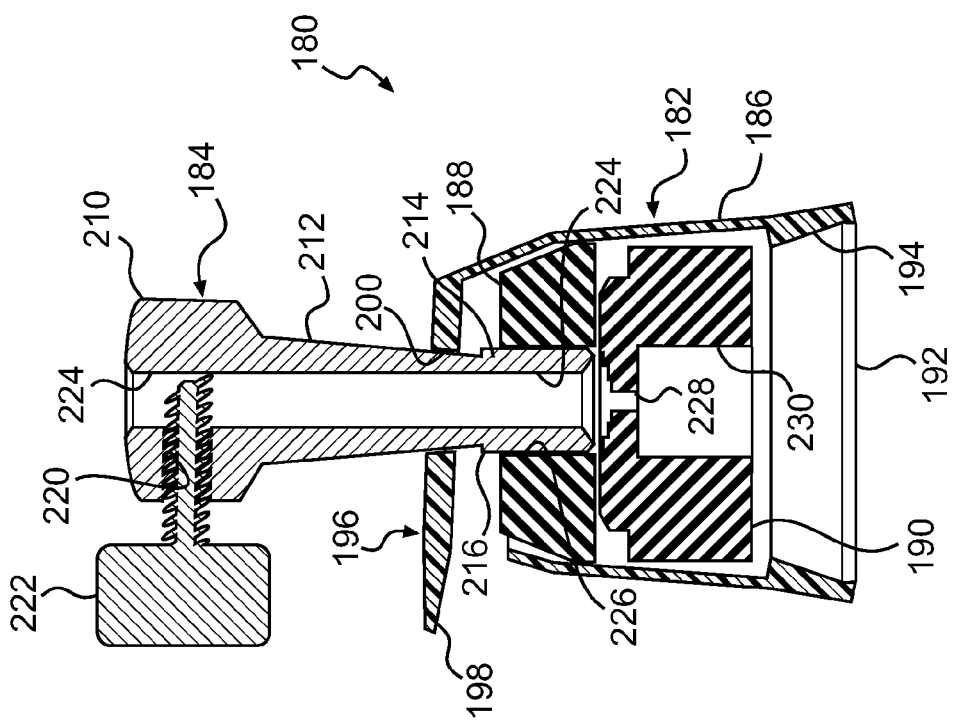
FIG. 18 shows a cross sectional view of the adapter valve of FIG. 9.
Figure 17:
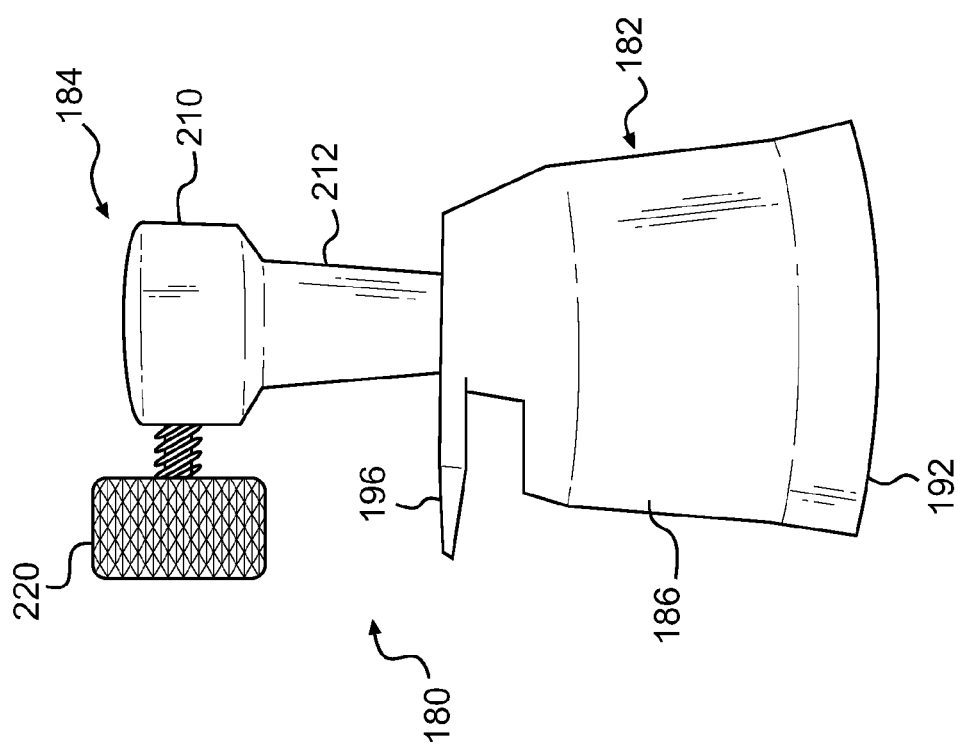
FIG. 17 shows an elevational view of an adapter valve.

FIGS. 17 and 18 show a modified needle adapter or valve 180 that will be placed on the access port on the endoscope to provide needle access into the endoscope and in this embodiment control over the length of the needle inserted. The adapter 180 is comprised of a lower portion 182 and an upper portion 184, with the lower portion 182 having an outer shell 186, preferably formed from rubber, or a plastic material, for example, one of those plastic materials as previously described herein above. The outer shell 186 of the adapter 180 also includes or encloses an upper insert 188 and a lower insert 190, and each is preferably formed from a compressible material, for example a rubber, an elastomeric material or other like material. A bottom portion of the outer shell 186 includes an opening 192 defined by an interior sloped wall 194 that ends at an internal shoulder that will snap fit over a mating portion of the endoscope. The outer shell 186 also includes a top portion 196 having a front tab 198 and a centrally located aperture 200.

The upper portion 184 includes a body preferably made from metal or, for example, a plastic like a polycarbonate, and has an enlarged top 210 from which a tapered middle portion 212 extends downwardly toward a slightly enlarged, cylindrically shaped bottom area 214 having a shoulder 216 defining a transition point between the tapered middle portion 212 and the bottom area 214. The top 210 includes a threaded aperture 220 that extends horizontally through a side of the top 210, or normal to bore 224, and receives therein a screw 222 that will be used to tighten against and secure a needle at a desired position. The, bore 224 extends vertically through the entire upper portion 184, is surrounded and defined by the side wall of that upper portion 184, and it is through that bore that a needle will be fed.

Insert 188 also includes a central aperture 226, in and through which the enlarged bottom area 214 is received, and insert 190 includes a first small central aperture 228, that will receive and provide a sliding seal around the exterior of an outer sheath of a needle, and a larger aperture 230 positioned there below that may be needed to fit over part of the access port of an endoscope.

The top portion 196 is attached to less than the whole of the circumference of the outer shell 186, preferably less than about half of that circumference, and tab 198, when pressed downwardly, will slightly displace and move aperture 200 into a more precise aligned condition with aperture 214 to enable or provide clear access for the bottom area 214 to pass there through, and will provide a grip by aperture 200 around the exterior of portion 212 when tab 198 is released thereby securely holding and supporting the upper portion 184 to the lower portion 182.

D. Operation

In use, needle 100 will preferably be longer than the length of tubing 72 of the chosen bronchoscope 70 so that an operating length can be determined and marked on outer sheath 170, indicating a point where screw 222 will be tightened. FIG. 3 shows the bronchoscope or endoscope 70 on which the valve adapter 180 has been mounted. Needle 100 has had its distal end threaded through bore 224, through the apertures 228 and 230, through the endoscope tubing 72 and partially beyond the distal end 78. At the point where a desired amount of the needle extends beyond distal end 78 the outer sheath 170 will be marked at the point knob 222 will be tightened against the sheath 170 of needle 100 to hold it in place. This tightening will be sufficient to hold the needle in place within adapter 180 but not enough to collapse the sheath 170 or to prevent movement of stylet 116, or the metal tube 138 there within. Alternatively, a point can be marked on the exterior of sheath 170 and the knob 222 can be unscrewed to permit needle 100 to be slightly retracted from tubing 72.

In either event, needle 150 will be pulled distally by unscrewing the upper and lower portions of leur-lock 124 and pulling metal tube 138 proximally which will pull outer needle 150 into hub 172, and inner needle 118 can be moved by loosening cap 114 on Y-connector 102 so that needle 118 lies totally within needle 150. The patient will be prepared and bronchoscope 70 will be put into place by inserting tubing 72 into a patient until, using ultra sound equipment to guide the placement of the bronchoscope with the distal end 78 being positioned at a desired location in the patient as shown in FIG. 2. At that point the balloon 60 can be inflated, the needle 100 can be again inserted to its desired position within valve adapter 180 and knob 222 tightened. The inner and outer needle 150 and 118 will be withdrawn into the distal end of outer sheath 170 and hub 172 and needle 100 can be threaded into and through tube 72 to the previously indicated point and screw 222 will be tightened down, making the distal end of needle 100 visible. The distal end of tube 72 can be appropriately positioned, if necessary, and the inner and outer needles 118 and 150 will be pushed distally into their extended positions to penetrate through the bronchial wall and into the lesion as shown at 64 with the end of outer sheath 170 and hub 172 lying against the bronchial wall Once the area 64 has been penetrated, stylet 116 can be pulled proximally to a position internally within outer needle 150. Then by loosening the upper portion 126 of leur-lock from the bottom portion 128 and by pulling and pushing the upper portion 126 back and forth outer needle 150 can be repeatedly inserted into and withdrawn from the patient's lesion or tissue to thereby collect cell, tissue and/or fluid specimens. During this process, a source of vacuum, for example a syringe 4, as shown in FIG. 3, can be attached to the Y-connector 102 thereby permitting a vacuum to be placed within needle 150 having passed through the whole length of needle 100 by having passed through tube 120, the interior of tube 138, tube 140 and directly into the interior of needle 150. This vacuum will assist in pulling tissue, cells and/or fluid into the hollow interior of needle 150 and beyond so that a desired quantity of tissue, cells and/or fluid can be collected from the patient without the need of withdrawing the needle 100 from the tubing 72, without withdrawing the stylet 116 from within needle 100, and with minimal discomfort to the patient. The vacuum can then be released and outer needle 150, along with the inner needle 118 will be withdrawn into hub 172. Needle 100 can then be withdrawn from within tube 72. Then the outer needle will be extended beyond hub 172 and over a desired receptacle the inner needle 118 can be pushed proximally thereby pushing out collected specimen tissue, fluid or other material from within outer needle 150. The released specimen material can be smeared onto slide, put into a 90% alcohol (a dry smear technique), or collected to a container by an NS solution (wet fluid technique). Then Needle 100 can be re-inserted into tube 72 and two or three additional specimen can be obtained using the same procedure outlined above.

In either event, needle 350 will be pulled proximally by unscrewing the upper and lower portions of leur-lock 324 and pulling metal tube 338 proximally which will pull wire 340 proximally that will in turn pull outer needle 350 into hub 372. The inner needle 318 can be moved relative to the outer needle 350 by loosening cap 314 on Y-connector 302 so that the inner needle 318 can be moved proximally and distally, depending upon the movement of cap 314. When both needles 318 and 350 are fully withdrawn into hub 372 needle 300 can be threaded into tube 72 which can then be inserted into a patient until, using ultra sound the distal end 78 is positioned at a desired location in the patient. At that point the balloon 60 can be inflated, the needle 300 can be again inserted to its desired position within valve adapter 180 and knob 222 tightened. At that point the inner needle 318 and the outer needle 350 can both be pushed distally to achieve the result shown in FIGS. 13 and 15 with needles 318 and 350 being able to penetrate an area like that shown at 64. Once the area 64 has been penetrated, stylet 316 can be pulled proximally to achieve the condition shown in FIG. 16. Then by loosening the upper portion 326 of leur-lock from the bottom portion 328, by pulling and pushing the upper portion 326 back and forth needle 350 can be repeatedly inserted into and withdrawn from the patient's tissue to thereby collect cell, tissue and fluid specimens. During this process, when cap 314 is in place sealing second portion 306, with the inner needle pushed distally, a source of vacuum, for example a syringe 4, as shown in FIG. 3, can be attached to the Y-connector 302 thereby permitting a vacuum to be placed within needles 318 and 350 having passed through the whole length of needle 300 by having passed through tube 320, the interior of tube 338, along wires 316 and 340, through aperture 364 and into the interior of needle 350. This vacuum will assist in pulling tissue, cells and/or fluid into the hollow interior of needle 350 and beyond so that a desired quantity of tissue, cells and/or fluid can be collected from the patient without the need of withdrawing the needle 300 from the tubing 72, without withdrawing the stylet 316 from within needle 300, and with minimal discomfort to the patient.

The vacuum can then be released and outer needle 350, along with the inner needle 318 will be withdrawn into hub 372. Needle 300 can then be withdrawn from within tube 72. Then the outer needle will be extended beyond hub 372 and over a desired receptacle the inner needle 318 can be pushed proximally thereby pushing out collected specimen tissue, fluid or other material from within outer needle 350. Further, a positive pressure can be provided from syringe 4 along the length of needle 300 and into both needles 318 and 350. The released specimen material can be smeared onto slide, put into a 90% alcohol (a dry smear technique), or collected to a container by an NS solution (wet fluid technique). Then needle 300 can be re-inserted into tube 72 and two or three additional specimen can be obtained using the same procedure outlined above.

When introducing elements of various aspects of the present invention or embodiments thereof, the articles "a," "an," "the" and "said" are intended to mean that there are one or more of the elements, unless stated otherwise. The terms "comprising," "including" and "having," and their derivatives, are intended to be open-ended terms that specify the presence of the stated features, elements, components, groups, and/or steps, but do not exclude the presence of other unstated features, elements, components, groups, and/or steps and mean that there may be additional features, elements, components, groups, and/or steps other than those listed. Moreover, the use of "top" and "bottom," "front" and "rear," "above," and "below" and variations thereof and other terms of orientation are made for convenience, but does not require any particular orientation of the components. The terms of degree such as "substantially," "about" and "approximate," and any derivatives, as used herein mean a reasonable amount of deviation of the modified term such that the end result is not significantly changed. For example, these terms can be construed as including a deviation of at least +/−5% of the modified term if this deviation would not negate the meaning of the word it modifies.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An endoscopic histology needle for collecting tissue, cell and/or fluid specimens from a patient, the endoscopic histology needle comprising:
    a needle assembly operatively connected to a multi-channel connector, the multi-channel connector having:
        a first section with a leur-lock connection at a first proximal end of the multi-channel connector,
        a second section with a leur-lock connection at a second proximal end of the multi-channel connector, and
        a distal portion, and
        an interconnecting structure that fluidly interconnects the first and second sections with the distal portion;
    the multi-channel connector first section having a first channel accepting a vacuum source and the multi-channel connector second section having a second channel for receiving a stylet in the multi-channel connector second section;
    the multi-channel connector distal portion having a distal end;
    a tubular member connected to the multi-channel connector distal end;
    a leur-lock assembly having an upper portion and a lower portion, the leur-lock assembly upper and lower portions being releasably connectable, the leur-lock upper portion having a hollow tubular interior attached to the multi-channel connector distal end so that the tubular member extends within said hollow tubular interior;
    the leur-lock lower portion having a hollow interior defined at least in part by an axially extending tube, the axially extending tube having a distal end;
    an inner tube having a proximal end secured to the tubular member and a distal end secured to a proximal end of an outer hollow needle;
    an exterior sheath having a proximal end and a distal end, the exterior sheath extending over the length of the inner tube with the exterior sheath proximal end being operatively connected to the distal end of the leur-lock lower portion axially extending tube;
    a hollow hub located at the exterior sheath distal end;
    the inner tube being slidingly positioned within the leur-lock lower portion hollow interior and the exterior sheath, and being movable within the leur-lock lower portion hollow interior, the exterior sheath to thereby slide the outer hollow needle axially within the exterior sheath and the hollow hub;
    the stylet having a proximal end and a distal end, the stylet proximal end being molded with a cap, and the stylet distal end being fixed to a proximal end of an inner needle that is slidingly positioned within the outer hollow needle, the stylet being movable within and passing through the second channel, through the tubular member and through the inner tube and into the interior of the outer hollow needle; and
    a fluid path extending from within the multi-channel connector, through the tubular member, through the inner tube and into the outer hollow needle.

2. The endoscopic needle as in claim 1 wherein the multi-channel connector has a Y shape.

3. The endoscopic needle as in claim 1 wherein the second section is axially aligned with the multi-channel connector distal portion.

4. The endoscopic needle as in claim 1 wherein the first portion is positioned at an angle to the multi-channel connector second section.

5. The endoscopic needle as in claim 4 wherein the angle varies from about 20° to about 90°.

6. The endoscopic needle as in claim 1 wherein the multi-channel connector has a hollow interior.

7. The endoscopic needle as in claim 1 wherein the inner needle is hollow.

8. The endoscopic needle as in claim 1 wherein the inner tube has a flexible distal section positioned between the outer needle and the tubular member.

9. The endoscopic needle as in claim 1 wherein the inner tube and the outer needle comprise a one piece structure.

10. The endoscopic needle as in claim 9 wherein the inner tube is a rigid metal tube.

11. The endoscopic needle as in claim 1 wherein the stylet has a distal end that extends into the outer needle.

12. The endoscopic needle as in claim 1 further including a stop member positioned at a desired location on the tubular member and wherein the leur-lock lower portion further includes a structure that will interact with the stop member.

13. The endoscopic needle as in claim 1 wherein the stylet includes a bent portion spaced proximally from the distal end thereof to control the extended condition of the inner needle relative to the outer needle.

* * * * *